(12) United States Patent
Yan et al.

(10) Patent No.: US 8,778,629 B2
(45) Date of Patent: Jul. 15, 2014

(54) STERILITY TEST METHOD AND TOTALLY ENCLOSED BACTERIAL AMPOULE INCUBATOR USED BY IT

(75) Inventors: Dan Yan, Beijing (CN); Xiaohe Xiao, Beijing (CN); Ping Zhang, Beijing (CN); Yongshen Ren, Beijing (CN); Cheng Jin, Beijing (CN)

(73) Assignee: 302 Military Hospital of China, Beijing (CN)

( * ) Notice: Subject to any disclaimer, the term of this patent is extended or adjusted under 35 U.S.C. 154(b) by 0 days.

(21) Appl. No.: 13/807,558

(22) PCT Filed: Jun. 28, 2011

(86) PCT No.: PCT/CN2011/001062
§ 371 (c)(1),
(2), (4) Date: Dec. 28, 2012

(87) PCT Pub. No.: WO2012/000309
PCT Pub. Date: Jan. 5, 2012

(65) Prior Publication Data
US 2013/0109052 A1 May 2, 2013

(30) Foreign Application Priority Data
Jun. 29, 2010 (CN) .......................... 2010 1 0211629

(51) Int. Cl.
*C12Q 1/22* (2006.01)

(52) U.S. Cl.
USPC .............................. 435/31; 435/34; 435/297.2

(58) Field of Classification Search
CPC .............. C12N 1/20; C12Q 1/04; C12Q 1/22; G01N 25/20
See application file for complete search history.

(56) References Cited

U.S. PATENT DOCUMENTS

2005/0221417 A1* 10/2005 Houghton et al. .............. 435/34
2009/0081721 A1* 3/2009 Meyer et al. .................... 435/34
2009/0317859 A1* 12/2009 Daniels et al. ................... 435/34

FOREIGN PATENT DOCUMENTS

| CN | 1772917 A | 5/2006 |
| EP | 1 785 722 A1 | 5/2007 |

OTHER PUBLICATIONS

McIlvaine P. et al., A Calorimetric Investigation of the Growth of the Luminescent Bacteria Beneckea Harveyi and Photobacterium Leiognathi, Biophysical Journal, 1977, vol. 17, pp. 17-25.*
Lee J. et al., Evaluation of the Heat Inactivation of *Escherichia coli* and *Lactobacillus plantarum* by Differential Scanning Calorimetry, Applied and Environmental Microbiology, Nov. 2002, vol. 68, No. 11, pp. 5379-5386.*
Olsen S.N. et al., Real-time quantification of microbial degradation of copepod fecal pellets monitored by isothermal microcalorimetry, Aquatic Microbial Ecology, Oct. 18, 2005, vol. 40, pp. 259-267.*
International Search Report issued in PCT/CN2011/001062 mailed Oct. 13, 2011 (6 pages).

* cited by examiner

*Primary Examiner* — Satyendra Singh
(74) *Attorney, Agent, or Firm* — Osha Liang LLP

(57) ABSTRACT

A sterility test method includes: selecting strain and culture medium, preparing bacterial cultures, transcribing fingerprint characteristics in thermograms as indices to verify the characteristics, drawing the thermodynamic parameters of the thermogram, determining the positive judgment index and performing sterility test for the samples. A fully-enclosed bacteria collecting ampoule incubator includes bacteria collecting ampoule system, sample and liquid feeding system and peristalsis liquid discharge system. The sample and liquid feeding system is connected with the bacteria collecting ampoule system by the liquid intake tube; and the bacteria collecting ampoule system is connected with the peristalsis liquid discharge system by the liquid drainage tube. The invention is characterized by short inspection time, high sensitivity, high automation and accurate test results on microbial contamination. It can also provide the overall process curve on the growth conditions. Such curve is provided with relatively favorable fingerprint, which enables qualitative analysis on the microbial contamination conditions.

2 Claims, 9 Drawing Sheets

STERILITY TEST METHOD AND TOTALLY ENCLOSED BACTERIAL AMPOULE INCUBATOR USED BY IT

This application is a National Stage Application of International Application Number PCT/CN2011/001062, filed Jun. 28, 2011; which claims priority to Chinese Application No. 2010/10211629.2, filed Jun. 29, 2010.

TECHNOLOGICAL FIELD

This invention relates to the field of inspections of sterile products, such as pharmaceuticals, foods, biological products and medical devices, specifically relates to sterile test methods and fully-enclosed bacteria collecting ampoule incubators for use with the methods.

BACKGROUND TECHNOLOGY

Sterility test is essential to ensure the safe use of sterile products as well as an important link to determine the production cycles of the sterile products. For example, in the pharmaceutical field, strict requirements have been formulated on the sterility tests for injections in the pharmacopeias in various countries. Such requirements essentially form the internationally consistent inspection standards and operation procedures, which have effectively enhanced the sterility guarantee levels of the preparations.

However, the current sterility test methods have certain limitations. First, the sterility test cycles are relatively long, limiting improvements in productivity of the enterprises. It is a common provision in pharmacopeias in various countries that the cultivation cycle of the sterility test shall be 14 days. If it is still impossible to judge the results, additional 7 days are required for subculture. If the result of "false positive" is detected, the tested shall be repeated. This may further extend the ex-factory waiting time and the production cycle. Secondly, the results of sterility test in current pharmacopeias are mainly made by visual observation of the turbidity of culture medium caused by the massive development of the microorganism, which is greatly influenced by the operation experience of the observers. The automation level is low, and there exists subjectivity to some extent. In addition, there are still risks to determine the sterilization conditions of the sample by the turbidity of the culture medium simply by visual operations: Turbidity not related to the growth of microorganism is difficult to be excluded in visual observation; and it is even more difficult to identify slowly developing microbial contamination that has not caused the turbidity of the culture medium within the specified inspection time. This may result in judgment of false positive or negative and affect the accuracy and reliability of the results.

In view of the above problems, it has been a focus of researches on sterile preparations domestically and abroad to establish a method for fast identification of the microbial contamination of the sterile preparation, to enhance the sensitivity and accuracy of the inspection, to shorten the inspection time, to enhance the automation level of the inspection and to supplement or replace the current methods. New methods such as microorganism laser light scattering method, bioluminescence inspection method, and PCR amplification inspection method have been established. These new methods have enhanced our ability to inspect microbial contaminations. However, the application of such methods are still restricted by factors such as the particle sizes of the microorganisms, interference from other particles, complicated operations, expensive instruments and preparations, or lack of universality of the methods (limited to certain types of microorganisms with narrow applications). Therefore, new inspection methods based on the life cycles and growth characteristics of microorganisms are needed.

According to theories of biothermodynamics, all biological activities are accompanied by metabolisms and transformations of energy and substance. Such energy may be monitored with a microcalorimetry system. A microcalorimetry system is a sensitive, fast, convenient, multichannel and real-time online monitoring instrument system. In recent years, the inventors' group has been using microcalorimetric methods to inspect the thermal effects during the growth of microorganisms for quality control and efficacy evaluation of medicines. Experience and results have been achieved to some extent. According to the studies, under proper conditions, the growth of a microorganism exhibits certain patterns and characteristics. Therefore, a new sterility test method may be established based on the microcalorimetric method.

Principles of this invention: Based on the functions available for the microcalorimeter to detect the thermal effects during the growth of the microorganism, transcribe the fingerprint characteristic thermograms for microorganisms of different survival conditions and different types in the microcalorimeter, and establish a standard archive for data analysis. Then transcribe the thermograms of the samples to be tested. On condition that the sterilization of the samples are not at all or not thoroughly made and is contaminated by microorganism, a trend of growth of microorganism may be represented in the thermogram for the sample. Compared with the standard archive established to quickly select the contaminated samples and preliminary determine the types of microorganisms that have contaminated the samples General operations of the microcalorimeter: Place the microorganism strain into the microcalorimetric ampoule for specific culture medium; then place the ampoule into the microcalorimeter detection channel; record the variations of the heat generated by the growth of the microorganism. However, when making sterile inspection with microcalorimeter, there exists a major defect in the operation links, which is, when conducting the sterility test, as the ampoule structure to be used together with the microcalorimeter is impossible to be sealed during the injection of the samples and culture mediums, which cannot meet the requirements in the microbial contamination inspection (sterility test) for the products of isolation with external environments (to avoid secondary contamination), enrichment of microorganisms and elimination of the antibacterial activity of the products. This may also cause the samples to be contaminated by external factors, leading to a judgment of false positive. Therefore, improvements are required on the ampoule of the microcalorimeter when making sterility test by the microcalorimetric method. Design guidelines for the fully-enclosed bacteria collecting ampoule incubator under this invention: (1) sterility: Apply suitable sterilization method to ensure the sterility of the bacteria collector; (2) tightness ensure effective isolation of the internal part of the system with external requirement (3) bacteria collection: equip necessary bacteria collection device for enrichment of microorganisms and elimination of the antibacterial activity of the products, equip suitable filter membranes according to the features of the samples to be tested; (4) thermal sensitivity: the system may enable sensitively detection of the heat generated by the growth and metabolism of the microorganism by the calorimeter; (5) pressure resistance: the system is able to meet the negative pressure requirements during the process of bacteria collection without damaging the microorganisms; (6) tolerance: the sample should be able to meet the requirements on sterility test on samples and be provided with sufficient inspection capacities; (7) simplicity: the system should be provided with convenient operations, high automation performance and functions of automatic result indication; (8) economy: the system should be economic and easily accessible and should be easy for batch production and generalization.

SUMMARY OF INVENTION

This invention aims to solve the defects in current sterility test methods that the cycle is relatively long, the sensitivity is low, the test results are greatly influenced by the operation experience of the observers, and fully-enclosed sterile operations are not available for the ampoule of micro calorimeters.

Technological solution of this invention for the abovementioned purposes, namely a sterility test method, involves the following steps:

(1) Prepare bacterial cultures: Culture different strains in a sterile culture medium to obtain bacterial culture with different concentrations and survival conditions for different strains as positive controls to transcribe (identify) fingerprint characteristic thermograms of the strains;

(2) Transcribe (identify) the fingerprint characteristic thermograms of each strain as diagnostic characteristics: place the bacterial culture obtained in Step (1) into a microcalorimeter; record the thermograms of the bacterial culture with varying concentrations and survival conditions for different strains, and obtain the fingerprint characteristic thermograms for the different strains;

(3) Extract the thermodynamic parameters of the thermograms obtained in Step (2) as indices for positive identification of the strains;

(4) Assess the sterility of the preparations to be tested: Filter the samples of the preparation to be tested; rinse the filtration products on the filter membrane with sterile cleaning liquid; mix the filtration products of the samples with culture medium; then place the mixture into the detection channel of the microcalorimeter; record the thermograms thereof; compare the fingerprint characteristic thermogram for different strains in Step (2) and the positive judgment indices for strains in Step (3), inspect whether there exists microbial contamination in the preparation to be tested.

Among the steps above, Step (1) to Step (3) are steps to establish test standards. After the fingerprint characteristic thermograms and related thermodynamic parameters for each strain are obtained and the positive identification indices for strains are established, such spectra and data formulae may be used as standards for further tests. In other words, the operations in Step (1) to Step (3) to establish standards need not be repeated, after the standards have been established. Only operation procedures in Step (4) are required on samples to be tested, followed with comparison with the standards so established.

Method to obtain the bacterial cultures of different concentrations for each strain in Step (1): Filter and wash the fresh strain culture to obtain an eluent; and dilute the eluent in 10-fold serial dilution with 0.9% sterile sodium chloride solution. The method to obtain different survival (growth) conditions of various strains: filter and wash the culture to obtain an eluent; place each eluent in refrigerator at −70° C. or in a water bath at 60° C. for 2 h, and dilute the eluent in 10-fold serial dilution with 0.9% sterile sodium chloride solution;

Specific methods to place the bacteria culture into the microcalorimeter in Step (2):

(2-1) Take the diluted cultures respectively of $10^{-3}$, $10^{-5}$, $10^{-7}$, $10^{-8}$, $10^{-9}$, $10^{-10}$, $10^{-11}$ concentrations for each strain from methods stated in Step (1);

(2-2) Place the diluted cultures of different concentrations at the same volume for each strain into a sterile culture medium, as a positive detection channel in the microcalorimeter;

(2-3) Use another aliquot of sterile culture medium as the blank control channel in the microcalorimeter.

The thermodynamic parameters indicated in Step (3) include: the time-dependent (varying with time), detection channel thermal power $P_i$, and the simultaneous (contemporary) blank control channel thermal power $P_0$, the maximum thermal power $P_{max}$, time required to reach the maximum thermal power $T_{max}$, total heat productivity $H_{total}$, and the slope k for each 15 min segment during the exponential growth of each curve.

Possible positive judgment (identification) indices for strains stated in Step (3): record the occurrence time for k≥0, which is the premise to determine the microbial contamination of the sample. At the same time, establish the positive judgment time index for the growth of the microorganism;

Method to determine the positive judgment time index of the microorganism growth: the time duration where the difference between the thermal power of the detection channel $P_i$ and the thermal power is $P_0$ greater than three times of the absolute value of $P_0$ is taken as the time point $(T_d)$ to detect the microbial contamination of the samples, which is: $T_d$=Time $[(P_i - P_0)/|P_0| \geq 3]$ When mixing the filtration products of the samples with the culture medium in Step (4), select the culture medium according to the conditions suitable for the growth of the strains.

When mixing the filtration products of the samples with the culture medium and placing the mixture into the ampoule of the microcalorimeter in Step (4), retain a gas environment that may boost fast growth of strains according to volume proportion in the ampoule.

Optimal solution: When placing the ampoule into the detection channel of the microcalorimeter in Step (4), set temperature of the detection channel in accordance with temperature suitable for the growth of the strains, which may be ranging from 23° C. to 37° C.

This invention also involves a fully-enclosed bacteria collecting ampoule incubator that enables the abovementioned methods, which includes the bacteria collecting ampoule system, the sample and liquid feeding system and the peristalsis liquid discharge system. The sample and liquid feeding system is connected with the bacteria collecting ampoule system by the liquid intake tube; and the bacteria collecting ampoule system is connected with the peristalsis liquid discharge system by the liquid drainage tube.

Bacteria collecting ampoule system involves ampoule bottle body. seal and fix the rubber sealing plug on the mouth of the ampoule bottle body; the liquid intake tube, liquid drainage tube and gas discharge tube are extended into the ampoule bottle body after penetrating the rubber sealing plug; provide a built-in filter in the ampoule bottle body; lay the filter membrane at the bottom of the filter; connect the top of the filter with the liquid intake tube mouth in the ampoule bottle; the liquid drainage tube mouth is extended to the bottom of the ampoule bottle across the filter, respectively install the liquid intake control, liquid discharge control valve and gas discharge control valve on the liquid intake tube, liquid drainage tube and gas discharge tube out of the ampoule bottle body; connect the air filter on top of the gas discharge tube.

The sample and liquid feeding system include the sample/ culture medium container and the liquid intake device with air filter;

The peristalsis liquid discharge system includes a peristaltic pump; connect the outlet of the peristaltic pump to the liquid discharge collector.

Install a liquid intake tube connector on the liquid intake tube between the liquid intake control and the sample and liquid feeding system; by disconnecting the tube connector, the sample and liquid feeding system may be separated from the bacteria collecting ampoule system; install the liquid drainage tube connector on the liquid drainage tube between the liquid discharge control valve and peristalsis liquid discharge system; by disconnecting the tube connector, the peristalsis liquid discharge system may be separated from the bacteria collecting ampoule system.

The liquid intake tube connector and liquid drainage tube connector are of plug type; the plugs of the liquid intake tube connector and the liquid drainage tube connector may be made butt joint to form the enclosed tube connector.

The body of the ampoule bottle is glass structure or hard transparent plastic structure with graduation line.

The liquid intake tube, liquid drainage tube and gas discharge tube are silica gel tubes; the liquid intake control, liquid discharge control valve and gas discharge control valve are Bayonet valves.

The gas discharge tube is stainless pinhead with air filtration device on the top.

The part of the liquid intake tube into the ampoule bottle body may be a diverging pipe thin on top and thick at bottom; the filter is fixed at the lower end of the diverging pipe. The external surface of the upper end of the diverging pipe is screw structure; an internal thread joint is fastened on the mouth of the liquid intake tube on the lower surface of the rubber sealing plug; the diverging pipe may be connected with such internal thread joint by the screw structure.

Compared with bacteria collection observation methods based on the current technologies, the microcalorimetric sterile method in this invention is provided with superiorities as follows:

① Detection time, microcalorimetric method is faster than observation method: the time required for microcalorimetric method detection is concentrated from 0 to 18 h, which that of bacteria collection observation method for positive characteristic is 10-36 h;

② Sensitivity, the microcalorimetric method is higher than the observation method: The microcalorimetric method may detect the growth of microorganism in dilution of lower than $10^{-10}$-$10^{-11}$ dilution; while the observation method cannot detect the growth of positive bacteria in dilution of the same conditions;

③ Quantifiability and differentiating competency of fingerprint characteristics, the microcalorimetric method is superior to the observation method: The microcalorimetric method may provide growth thermograms, quantitive thermodynamic parameters and standard formulas for the detection and judgment of positive bacteria with fingerprint characteristics for the microorganism strains; while the observation method judges the turbidity of the culture medium just by visual observations, which is provided with no quantitive features and without the judgment features for strains;

④ Automation level and accuracy, the microcalorimetric method is superior to the observation method: the microcalorimetric method can detect and record the heat metabolism of the growth of the microorganism with flexible and accurate methods; and it can also report the positive inspection results by analyzing the thermodynamic parameters, representing a high level of automation; meanwhile, it can also avoid the increment of workload and risk of secondary contamination caused by repeated manual interference and observation in traditional bacteria collection observation method as well as false positive judgment on turbidity of culture medium caused by the growth of non-microorganism (for example, turbidity caused by mixture of medicine and culture medium) and false negativity that the growth of microorganism is hard to cause turbidity of the culture medium (for example, during the growth of *Candida albicans* and *Bacillus subtilis*, it is hard to cause obvious turbidity of the culture medium in a short time, and the results is relatively difficult to be determined) by traditional observation methods.

Compared with the traditional microcalorimetric ampoule, the fully-enclosed bacteria collecting ampoule incubator may achieve the enrichment of the microorganism for the sterile (bacteria collection function) in a fully-enclosed sterile system, eliminate the bacteriostatic activity interference of the samples by rinsing the membrane (anti-interference function), recover the microorganism by adding the culture medium (cultivation function) and record the heat metabolism conditions of the growth of the microorganism by placing the calorimeter channel (recording function). The possibility of contamination on samples or culture mediums by external factors is eliminated of the overall process from sampling to cultivation. Also, the possibility of misjudgment of positive samples (false positive) is also eliminated. The accuracy of the detection is obviously enhanced.

Compared with the current sterility test bacteria collecting incubator, the fully-enclosed bacteria collecting ampoule incubator under this invention has superiorities as follows:

① This invention may be applied in the microcalorimetric method sterility test, while the current sterility test bacteria collector is suitable only for general observation methods;

② The current bacteria collecting incubator mainly depends on visual observations, which is provided with disadvantages of repeated observation (14 days), great workload and high labor costs. This invention applies microcalorimeter to record the variations of the heat metabolism on the growth of the microorganism in a real-time, on-line, multichannel and automatic manner. This enables high automation and can reduce the labor intensity and cost;

③ By adopting the microcalorimetric method of this Invention, the heat metabolism of the microbial contaminants in the sample may be detected, which enables judgment of the microbial contamination in a more flexible and quick manner; compared with the current bacteria collecting incubator which depends mainly on visual observation to detect the turbidity of the culture medium, this invention may detect the microbial contamination in early stages, which saves the detection time;

④ By adopting the microcalorimetric method of this Invention, the heat metabolism of the microbial contaminants in the sample may be detected; with reference to the quantitive judgment formulas for the sterile conditions of the samples, the sterile conditions of the samples may be judged in an accurate and quantitive manner; compared with the current bacteria collecting incubator which depends mainly on visual observation to detect the turbidity of the culture medium, this invention provides a more accurate method that can effectively avoid the possible misjudgment on the results by visual observations;

⑤ By adopting the microcalorimetric method of this Invention, overall process record may be made on the heat metabolism curve of the microbial contaminant of the samples, which is provided with fingerprint characteristic to some extent; Compared with the current observation methods where results can only be judged by visual observations, it may provide more comprehensive information and may be applied in the preliminary verification of the types of microorganism contaminants.

BRIEF DESCRIPTIONS OF THE DRAWINGS

Figure 1:
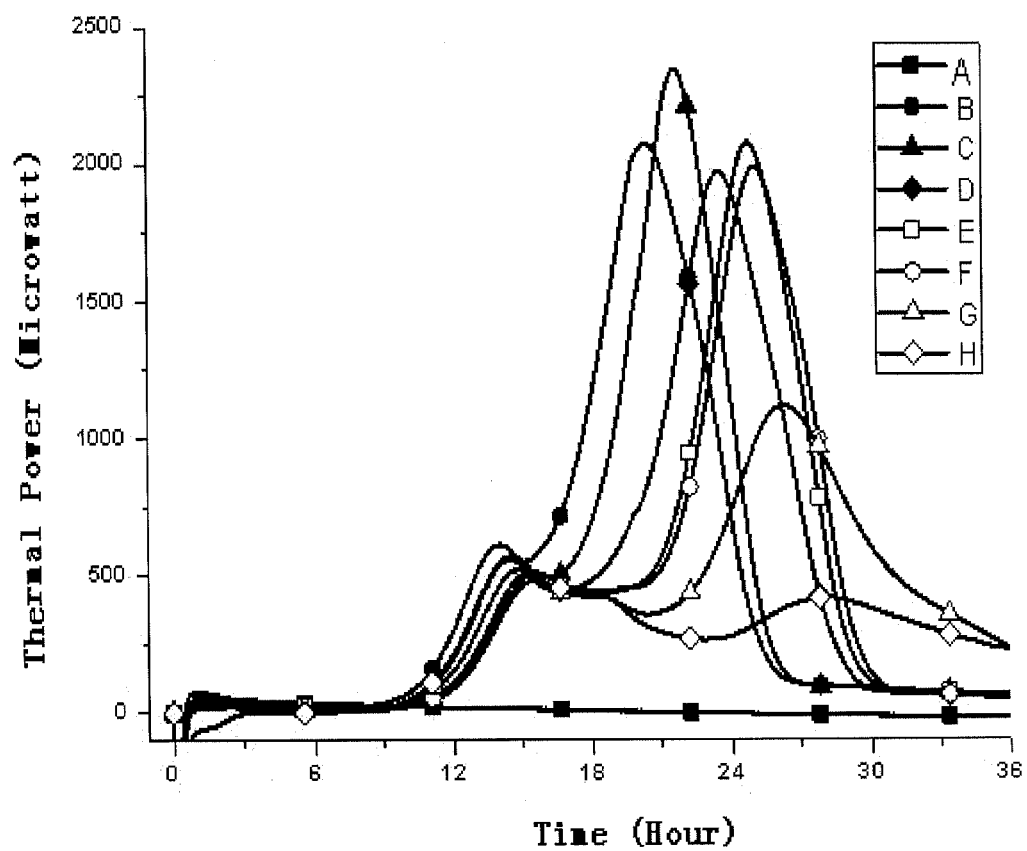
FIG. 1 is the growth spectrum of Staphylococcus aureus of different concentrations transcribed by method under this invention.
Figure 2:
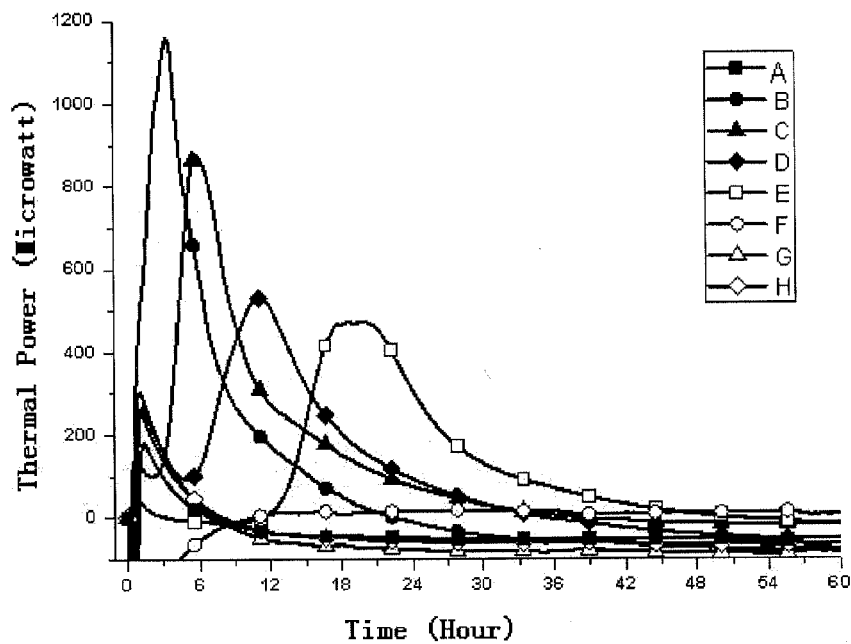
FIG. 2 is the growth spectrum of Escheichia coli of different concentrations transcribed by method under this invention.
Figure 3:
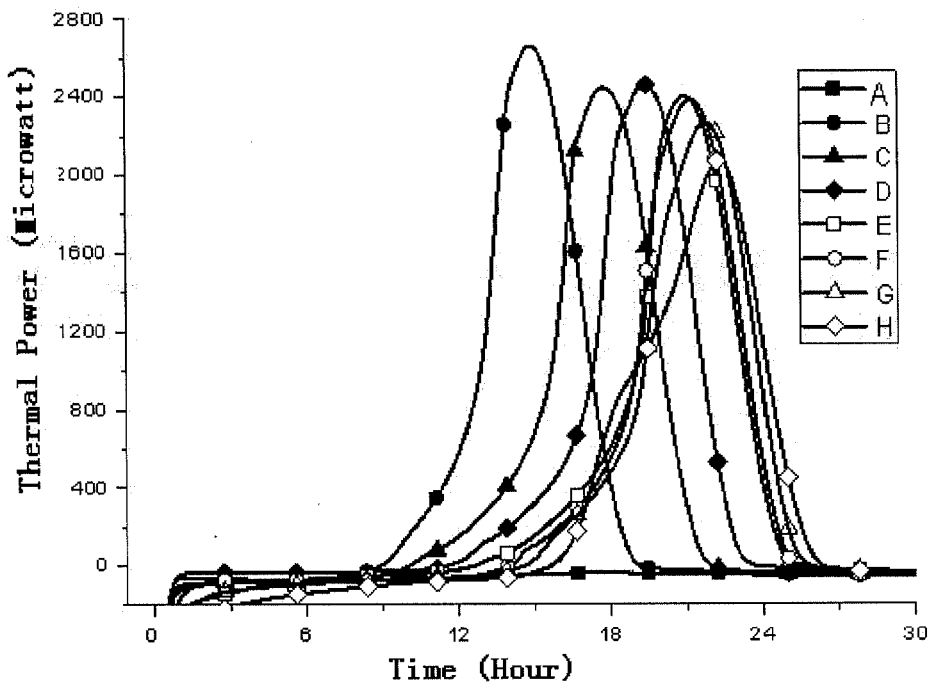
FIG. 3 is the growth spectrum of Pseudomonas aeruginosa of different concentrations transcribed by method under this invention.
Figure 4:
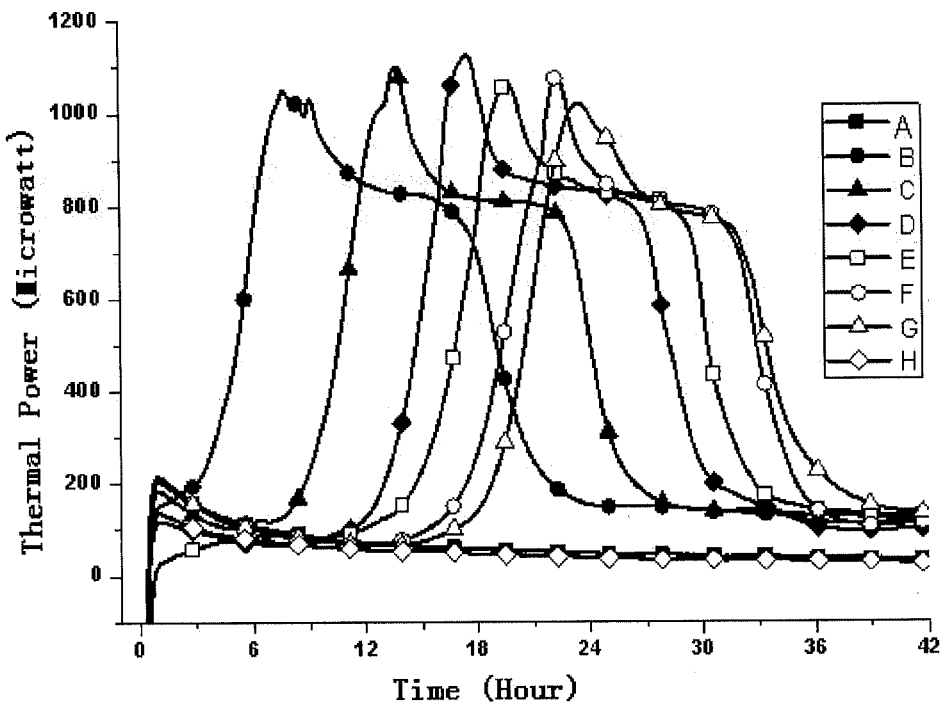
FIG. 4 is the growth spectrum of Clostridium sporogenes of different concentrations transcribed by method under this invention.
Figure 5:
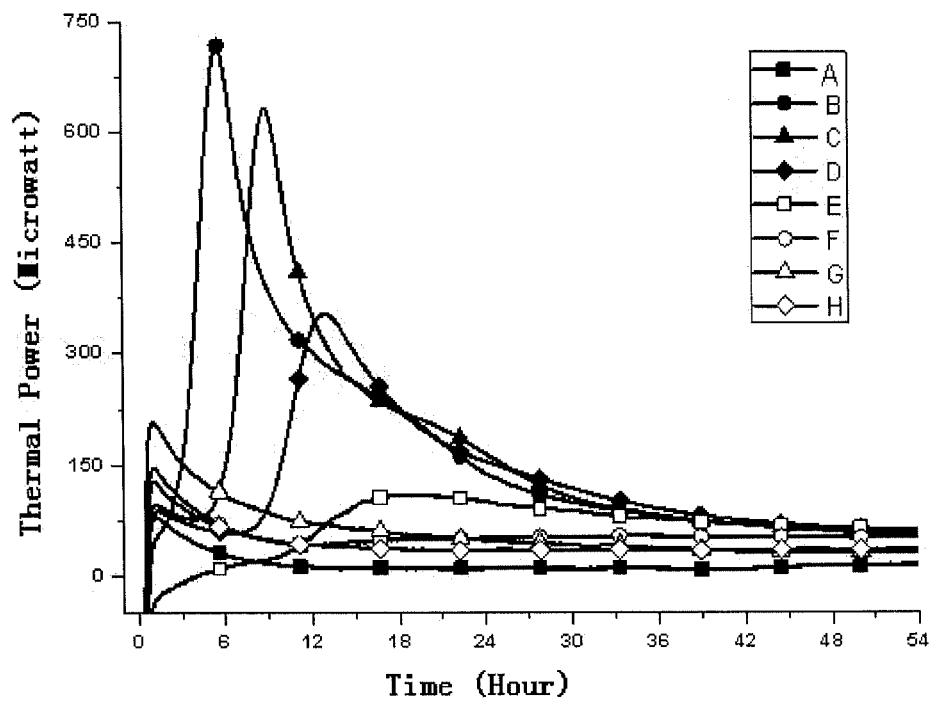
FIG. 5 is the growth spectrum of Shigella dysenteriae of different concentrations transcribed by method under this invention.
Figure 6:
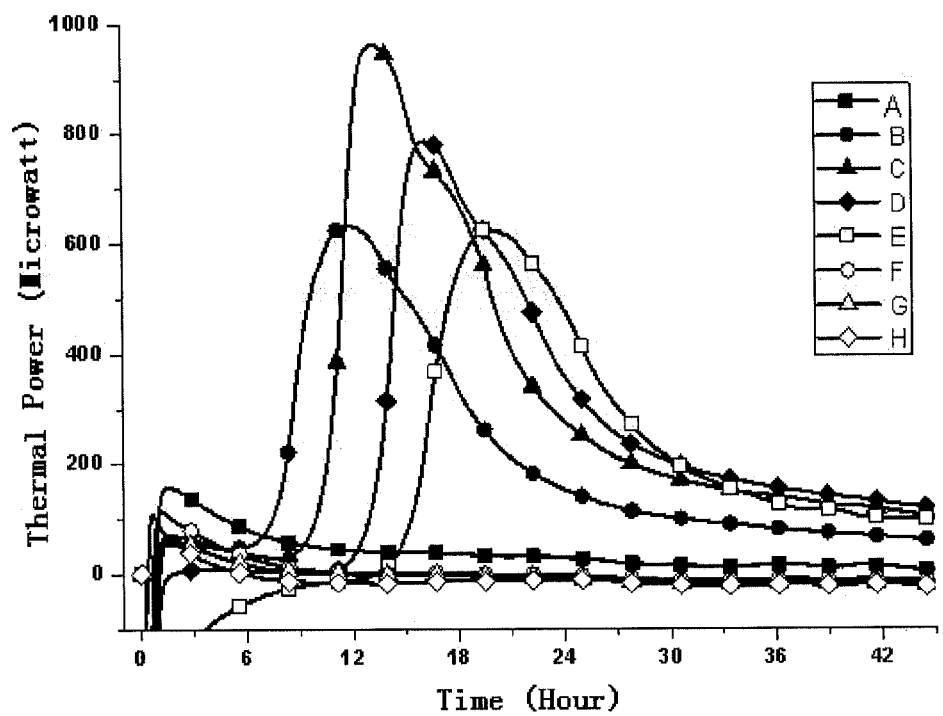
Figure 7:
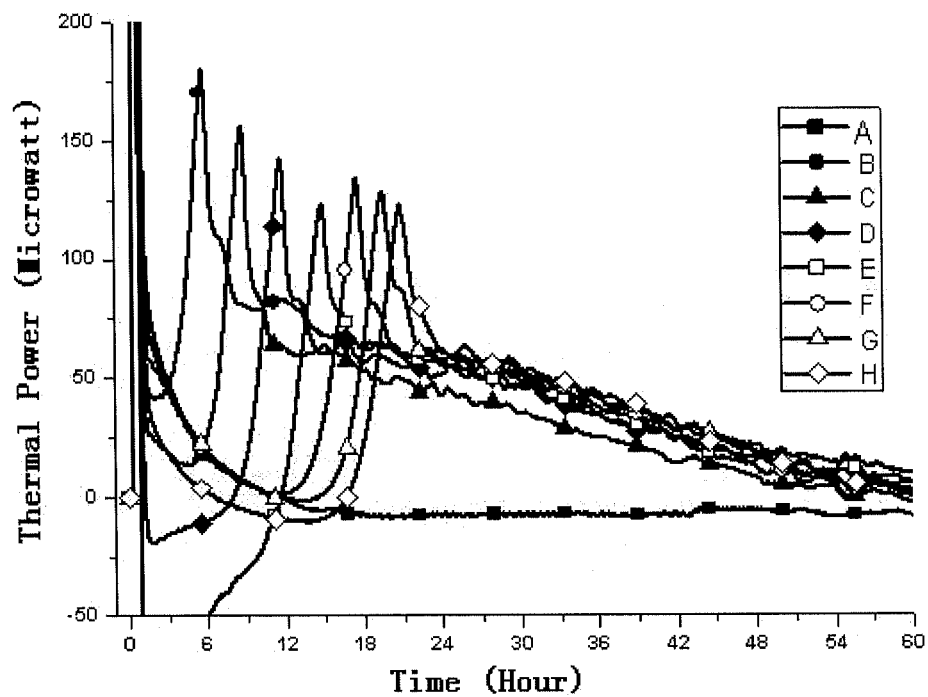
Figure 8:
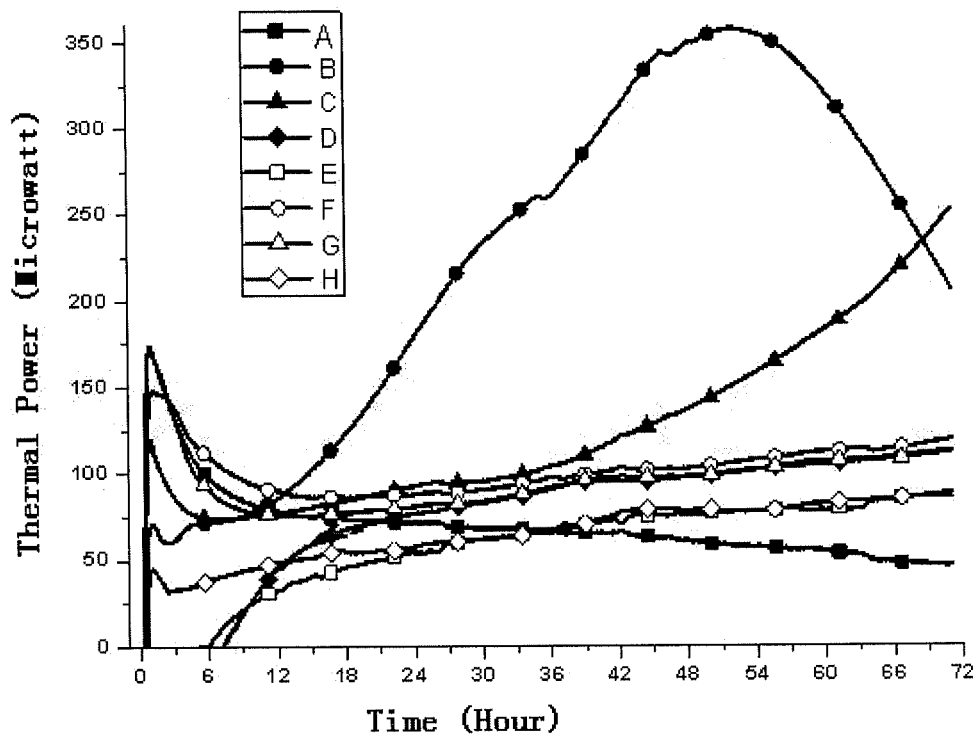
Figure 9:
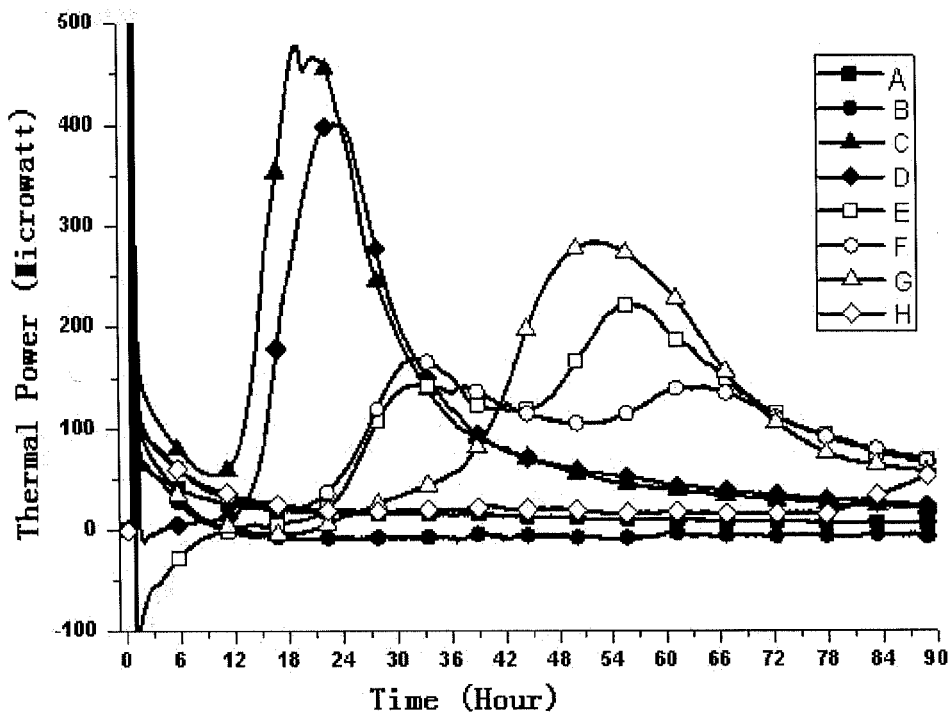
Figure 10:
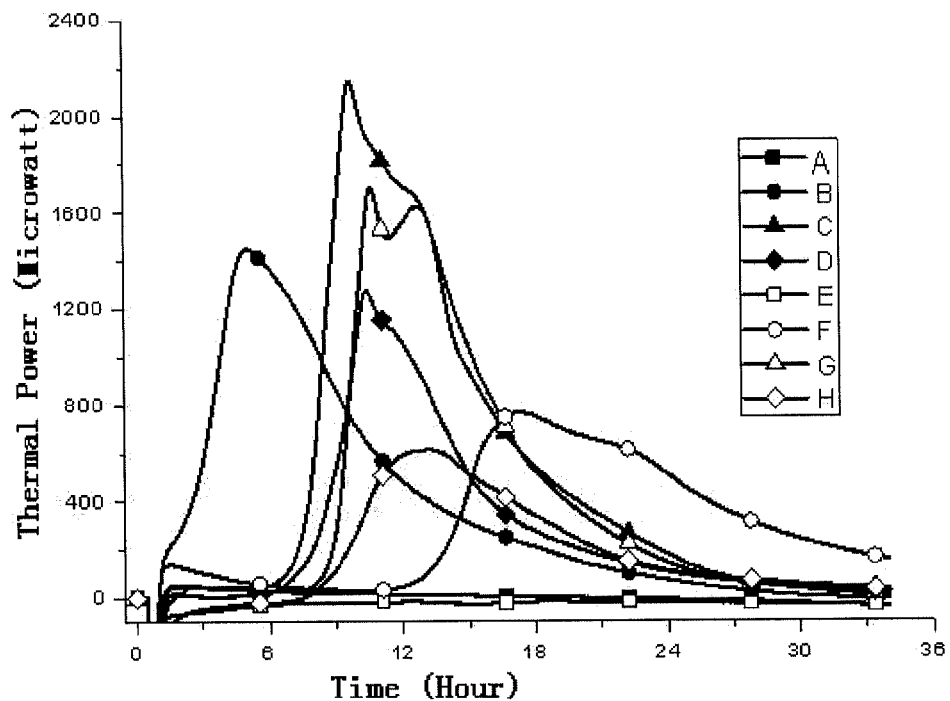
Figure 11:
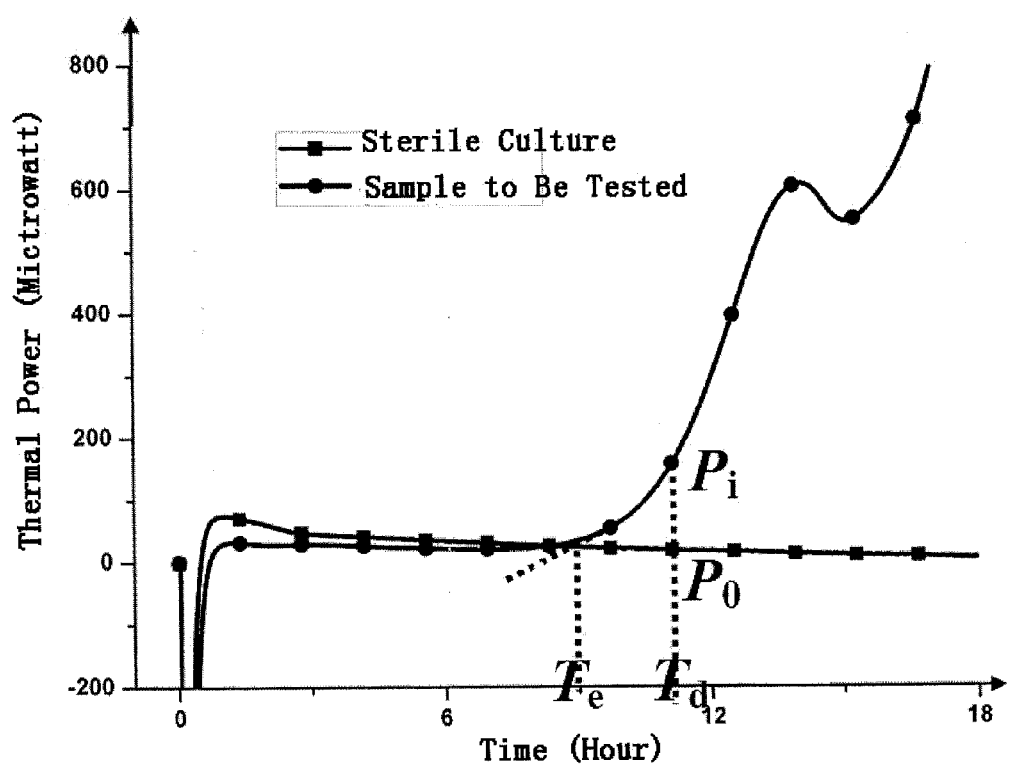
Figure 12:
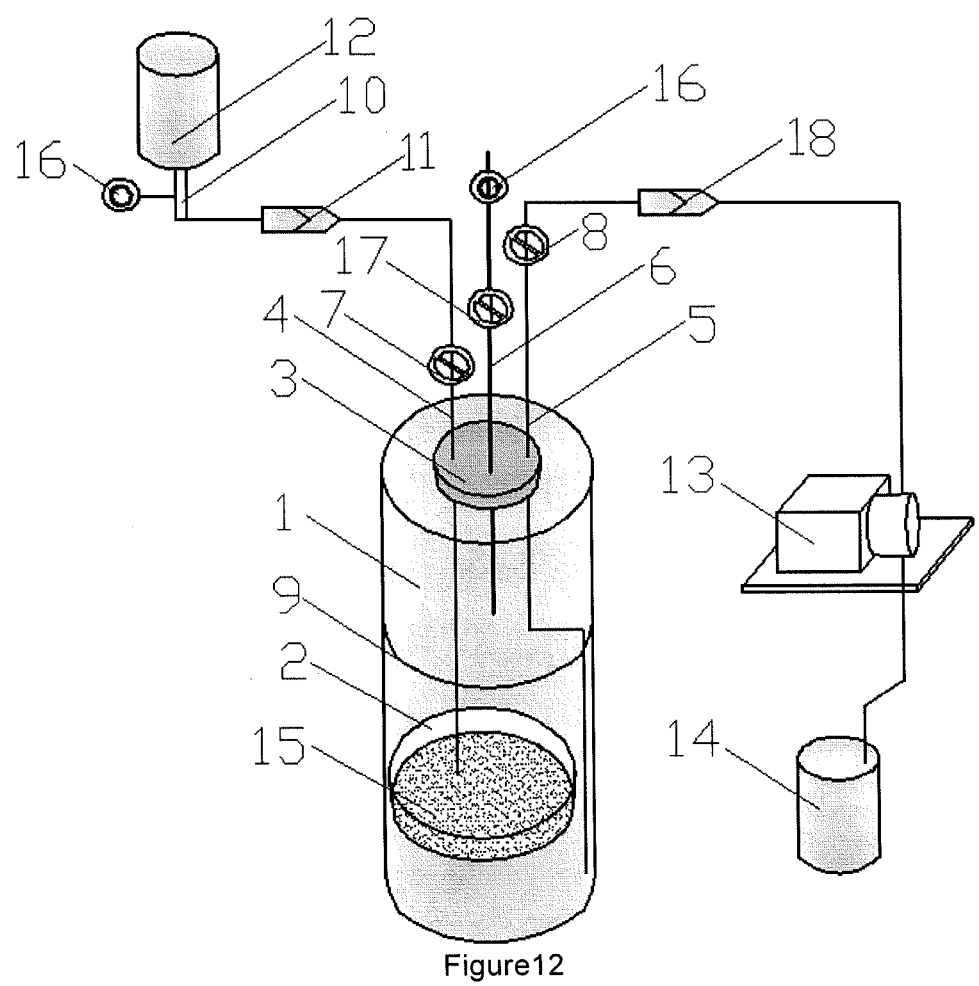
Figure 13:
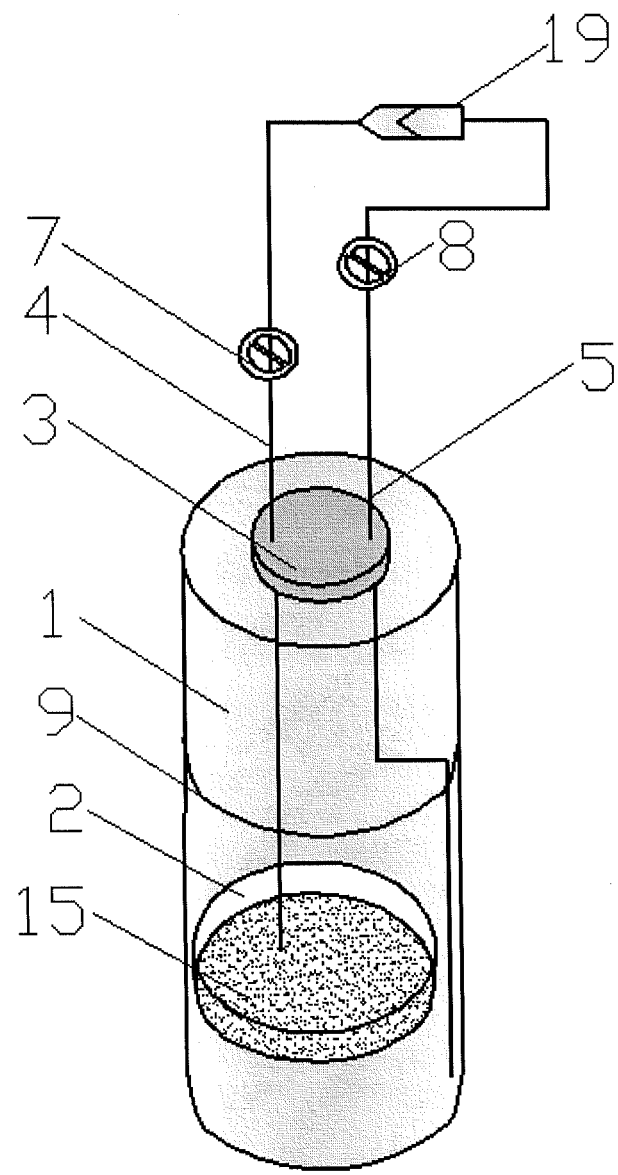
Figure 14:
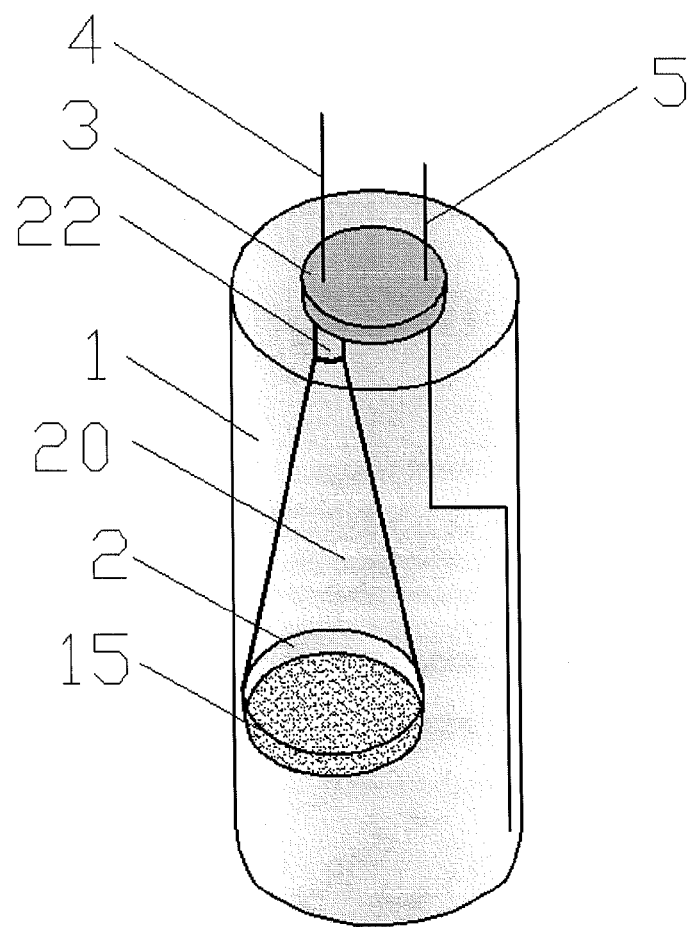
Figure 15:
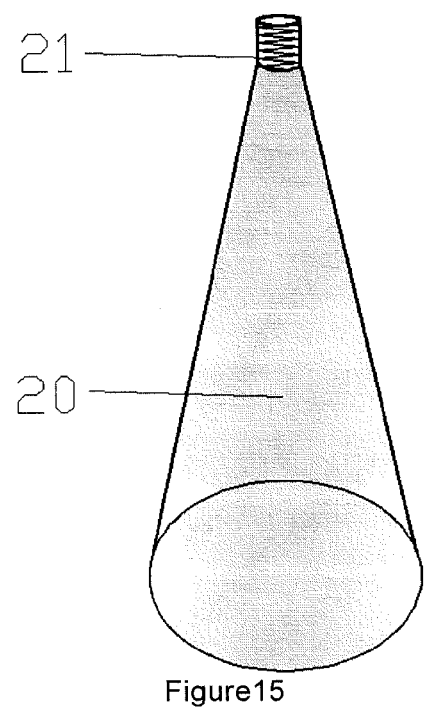

FIG. 6 is the growth spectrum of Bacillus subtilis of different concentrations transcribed by method under this invention; Where, A: sterile fluid thioglycollate culture medium; B: $10^{-3}$ dilution; C: $10^{-5}$ dilution; D: $10^{-7}$ dilution; E: $10^{-8}$ dilution; F: $10^{-9}$ dilution; G: $10^{-10}$ dilution; H: $10^{-11}$ dilution;

FIG. 7 is the growth spectrum of Aspergillus niger of different concentrations transcribed by method under this invention;

FIG. 8 is the growth spectrum of Candida albicans of different concentrations transcribed by method under this invention; Where, A: sterile Modified martin medium; B: $10^{-3}$ dilution; C: $10^{-5}$ dilution; D: $10^{-7}$ dilution; E: $10^{-8}$ dilution; F: $10^{-9}$ dilution; G: $10^{-10}$ dilution; H: $10^{-11}$ dilution;

FIG. 9 is the growth spectrum of Staphylococcus aureus of different concentrations transcribed by method under this invention; Where, A: sterile fluid thioglycollate culture medium; B: sterile physiological saline; C: 35° C. $10^{-5}$ dilution; D: 35° C. $10^{-7}$ dilution; E: −70° C. $10^{-5}$ dilution; F: −70° C. $10^{-7}$ dilution; G: 60° C. $10^{-5}$ dilution; H: 60° C. $10^{-7}$ dilution;

FIG. 10 is the thermogram for sterility test with method under this invention for compound herba artemisiae injection under different sterilization conditions; Where, A: normal sample+fluid thioglycollate culture medium: Staphylococcus aureus+fluid thioglycollate culture medium; C: unsterilized sample+fluid thioglycollate culture medium; D: sub-sterilized samples+fluid thioglycollate culture medium; E: normal sample+Modified martin medium; F: Candida albicans+ Modified martin medium; G: non-sterilized samples+Modified martin medium; H: sub-sterilized samples+Modified martin medium;

FIG. 11 is the schematic of the relations of the parameters of the positive judgment indices with method under this invention, Where, $P_i$: thermal power of the sample to be tested; $P_0$: sterile culture medium thermal power simultaneously occurred with $P_0$; k: the offsetting of the thermogram for every 15 min; $T_e$: occurrence time of index growing period k≥0 (Time of exponential growth); $T_d$: time to detect the positive sample microbial contamination (Time of Detection);

FIG. 12 is the structural diagram for the fully-enclosed bacteria collecting ampoule incubator under this invention;

FIG. 13 is the structural diagram of the fully-enclosed bacteria collecting ampoule incubator structural diagram based on the enclosed tube connector formed by butt-joint of the liquid intake tube connector and the liquid drainage tube connector plug with the gas discharge tube removed;

FIG. 14 is the structural diagram of the diverging pipe deformed from the part of liquid intake tube extended into the ampoule bottle body;

FIG. 15 is the structural diagram of the diverging pipe; Where, 1, ampoule bottle body; 2, filter; 3, rubber sealing plug; 4, liquid intake tube; 5, liquid drainage tube; 6, gas discharge tube; 7, liquid intake control; 8, liquid discharge control valve; 9, graduation line; 10, liquid intake device; 11, liquid intake tube connector; 12, sample/culture medium container; 13, peristaltic pump; 14, liquid discharge collector; 15, filter membrane; 16, air filter; 17, gas discharge control valve; 18, liquid drainage tube connector; 19, enclosed tube connector; 20, diverging pipe; 21, screw structure on the upper end of the diverging pipe; 22, the internal threaded coupling of the rubber sealing plug

DETAILED DESCRIPTION

The technological solution under this invention is not limited to the specific implementation methods listed hereinafter, and involves random combinations among such specific implementation methods.

Specific Implementation Method I: Inspection method for the sterility of the sterile preparation provided in this invention involves the following steps:

I. Experimental Materials

1, Medicines and Reagents: Compound herba artemisiae injection (50 mL/bottle, Batch No.: 20100120), including normal samples (Norm-sterilized Samples, Norm-SS), non-sterilized samples (Non-sterilized Samples, Non-SS), sub-sterilized samples (Sub-sterilized Samples, Sub-SS) (100° C. flowing steam sterilization for 10 min), all provided by the Pharmaceutical Department of 302 Military Hospital of China.

2, Instruments and Materials: Type 3114 TAM air isothermal microcalorimeter (Isothermal microcalorimeter) (TA Instrument, US), TAM Assistant Workstation, with a detectability of 4 µW, 24 h baseline shift smaller than ±20 µW, detection range of ±600 mW, working temperature of 5-90° C. SW-CT-2FD two-man one-sided clean bench (Suzhou Purification Equipment Factory); NS01-2 fully-enclosed sterile test filtration incubator (Beijing Niuniu Gene Technology Co., Ltd., Batch No. 20090910); TH2-22 bench-type Constant Temperature Vibrator (Jiangsu Taicang Experiment Equipment Factory); HTY-III Intelligent Bactria Collector (Hangzhou Tailin Medical Equipment Co., Ltd.); 303AB-6 Water jacket Incubator (Shanghai Shuli Instrument Co., Ltd.), 0.45 µm cellulose acetate ester micropore filter membrane (Beijing Chemical Factory), 0.9% sterile sodium chloride solution (Shijiazhuang No. 4 Pharmaceutical. Co., Ltd.).

3, Strains and culture mediums of [Staphylococcus aureus (S. aureus), CMCC(B) 26003], [Escheichia coli (E. coli), CMCC(B) 44102], [Pseudomonas aeruginosa (P. aeruginosa), CMCC(B) 10104], [Shigella dysenteriae, (S. dysenteriae), CMCC(B) 51252], [Bacillus subtilis (B. subtilis), CMCC(B) 63501], [Clostridium sporogenes (C. sporogenes), CMCC(B) 64941], [Candida albicans (C. albicans), CMCC (F) 98001], [Aspergillus niger (A. niger), CMCC(F) 98003], all provided by the National Institute of Control of Pharmaceutical and Biological Product; [Thioglycollate medium (TM), (hereinafter referred to as "TM"), Batch No.: 091020], [Modified martin medium (MMM), (hereinafter referred to as "Martin"), Batch No.: 090915], (Nutrient Broth Medium, Batch No.: 090922), (Powered Agar, Batch No.: 091022), (Sodium Rose Bengal Medium, Batch No.: 090912), (Peptone, Batch No.: 090708), all purchased from the National Institute of Control of Pharmaceutical and Biological Products.

II, Preparation of Bacteria Culture

Inoculate the fresh cultures of Staphylococcus aureus, Escheichia coli, Pseudomonas aeruginosa, Shigella dysenteriae, Bacillus subtilis into the nutrient broth; inoculate the fresh cultures of Clostridium sporogenes into the culture medium of TM carbonate and cultivate under 30-35° C. for 18-24 h; inoculated the fresh cultures of the Candida albicans into the culture medium of modified Martin agar and cultivate under 23-28° C. for 24-48 h; dilute the abovementioned cultures to 10-fold with 0.9% sterile sodium chloride solution, and obtain the bacteria suspension liquid with the bacteria concentration smaller than 100 cfu·mL$^{-1}$;

Inoculate fresh cultures of the Aspergillus niger into the inclined plane of the culture medium of the modified Martin agar, cultivate under 23-28° C. for 5-7 days, apply 3-5 mL sterile sodium chloride solution of 0.9% to elute the spores. Dilute the eluent to 10-fold with 0.9% sterile sodium chloride solution, and obtain the spore suspension liquid with the spore concentration smaller than 100 cfu·mL$^{-1}$;

Take fresh Staphylococcus aureus culture of 5 mL, and keep it respectively for 2 h in −70° C. refrigerator and 60° C. water bath; dilute to 10-fold with sodium chloride solution of 0.9%.

The diluted solutions of different concentrations for the microorganism are taken as the positive control of the sterility test.

III, Obtaining the Fingerprint Characteristic Thermogram for the Strain

Take the diluted cultures of $10^{-3}$, $10^{-5}$, $10^{-7}$, $10^{-8}$, $10^{-9}$, $10^{-10}$, $10^{-11}$ for each strain, 1 mL respectively; inject into the microcalorimeter ampoule respectively; guide into the corresponding sterile culture medium of 9 mL respectively as the positive detection channel; take another ampoule to directly guide the corresponding sterile culture medium as the blank control channel.

Add the fluid thioglycollate culture medium into the diluted cultures of the Staphylococcus aureus, Escheichia coli, pseudomonas aeruginosa, Bacillus subtilis, Clostridium sporogenes, Dysentery bacterium; place them into the 35° C. microcalorimeter; record the thermogram (heat flow) for each strain; add modified martin medium into the diluted cultures of the Candida albicans and Aspergillus niger; place into the 28° C. microcalorimeter; record the thermogram for each strain, as shown in FIG. 1 to FIG. 8.

Take fresh cultures of the Staphylococcus aureus; respectively inject 1 mL of culture stored under −70° C. and the diluted culture solution of $10^{-5}$, $10^{-7}$ stored under 60° C. into the microcalorimeter ampoule; then respectively introduce 9 mL sterile fluid thioglycollate culture medium as the detection channel for microorganism under different conditions; the taken two additional ampoules and respectively introduce the sterile fluid thioglycollate culture medium and sterile physiological saline, 10 mL respectively, as the blank control channel. Respectively place the ampoules into the 35° C. microcalorimeter; record the thermogram of each strain, as shown in FIG. 9.

IV. Identifying the Thermodynamic Parameters of the Thermogram determining the positive judgment indices for strains: detection channel thermal power $P_i$ varying according to the time and the simultaneous blank control channel thermal power $P_0$, the maximum thermal power $P_{max}$, time required to reach the maximum thermal power $T_{max}$, total heat productivity $H_{total}$, and the offsetting k for each 15 min of each exponential growth of the curve; record the occurrence time of k≥0 (Time of exponential growth, $T_e$).

Identifying the thermodynamic parameters for each curve;

Parameters identified under different concentration conditions are shown as follows, where, Dilution: dilution; cfu: colony forming unit; $T_e$: occurrence time of k≥0; k: the offsetting for each 15 min of the thermogram; $T_d$: detection time of the microorganism; $P_i$: thermal power of the growth of the bacteria culture under different concentrations; $P_0$: sterile culture medium thermal power simultaneous to $P_i$; $P_{max}$, maximum thermal power; $T_{max}$, time to reach maximum thermal power; $H_{total}$, total thermal power.

TABLE 1A

Thermodynamic Parameters for Growth of Staphylococcus aureus of Different Concentrations

| Dilution | cfu | $T_e$ (h) | K (min$^{-1}$) | $T_d$ (h) | $P_0$ (μW) | $P_i$ (μW) | $P_{max}$ (μW) | $T_{max}$ (h) | $H_{total}$ (μJ) |
|---|---|---|---|---|---|---|---|---|---|
| 0 | 0 |  | −0.005 |  |  |  | 74.900 | 1.011 | 279.746 |
| $10^{-3}$ | $10^7$ | 8.25 | 0.0155 | 10.300 | 21.092 | 84.450 | 2079.002 | 20.453 | 15521.674 |
| $10^{-5}$ | $10^5$ | 8.75 | 0.0104 | 10.539 | 18.501 | 74.161 | 2349.857 | 21.658 | 14630.561 |
| $10^{-7}$ | 765 | 8.75 | 0.0121 | 10.864 | 19.507 | 78.052 | 1977.391 | 23.575 | 15214.055 |
| $10^{-8}$ | 75 | 5.25 | 0.0241 | 10.994 | 20.520 | 82.263 | 2082.762 | 24.786 | 14686.436 |
| $10^{-9}$ | 10 | 8.25 | 0.0146 | 11.206 | 20.258 | 81.255 | 1995.019 | 25.056 | 14885.644 |
| $10^{-10}$ | 1 | 9.00 | 0.0092 | 11.594 | 18.757 | 75.323 | 1123.599 | 26.297 | 13852.769 |
| $10^{-11}$ | <1 | 9.25 | 0.0125 | 11.772 | 18.205 | 72.940 | 570.219 | 27.558 | 9176.494 |

TABLE 1B

Thermodynamic Parameters for Growth of Escheichia coli of Different Concentrations

| Dilution | cfu | $T_e$ (h) | K (min$^{-1}$) | $T_d$ (h) | $P_0$ (μW) | $P_i$ (μW) | $P_{max}$ (μW) | $T_{max}$ (h) | $H_{total}$ (μJ) |
|---|---|---|---|---|---|---|---|---|---|
| 0 | 0 |  | −0.0049 |  |  |  | 179.871 | 1.367 | −2145.798 |
| $10^{-3}$ | $10^5$ | 0.75 | 1.3062 | 0.817 | −192.291 | 390.713 | 1156.069 | 3.358 | 4668.304 |
| $10^{-5}$ | $10^3$ | 2.25 | 0.0432 | 3.697 | 70.112 | 280.515 | 876.261 | 5.806 | 7049.632 |
| $10^{-7}$ | 38 | 5.25 | 0.0172 | 5.469 | 24.478 | 98.313 | 530.565 | 11.122 | 5459.391 |

TABLE 1B-continued

Thermodynamic Parameters for Growth of *Escheichia coli* of Different Concentrations

| Dilution | cfu | $T_e$ (h) | K (min$^{-1}$) | $T_d$ (h) | $P_0$ (μW) | $P_i$ (μW) | $P_{max}$ (μW) | $T_{max}$ (h) | $H_{total}$ (μJ) |
|---|---|---|---|---|---|---|---|---|---|
| $10^{-8}$ | 4 | 9.00 | 0.0058 | 13.508 | −39.752 | 79.687 | 472.617 | 19.956 | 6097.893 |
| $10^{-9}$ | <1 | 12.00 | 0.0100 | 23.372 | −8.231 | 16.758 | 18.491 | 28.019 | 635.264 |
| $10^{-10}$ | <1 | | −0.0078 | ND | | | 303.623 | 1.028 | −3284.053 |
| $10^{-11}$ | <1 | | −0.0076 | ND | | | 251.221 | 1.144 | −2305.055 |

ND: Not detected

TABLE 1C

Thermodynamic Parameters for Growth of *Pseudomonas aeruginosa* of Different Concentrations

| Dilution | cfu | $T_e$ (h) | K (min$^{-1}$) | $T_d$ (h) | $P_0$ (μW) | $P_i$ (μW) | $P_{max}$ (μW) | $T_{max}$ (h) | $H_{total}$ (μJ) |
|---|---|---|---|---|---|---|---|---|---|
| 0 | 0 | | −0.0077 | | | | −71.591 | 8.389 | −1611.395 |
| $10^{-3}$ | $10^5$ | 3.25 | 0.0025 | 9.833 | −64.897 | 130.250 | 2664.904 | 14.925 | 9905.841 |
| $10^{-5}$ | 2500 | 4.00 | 0.0109 | 11.614 | −57.866 | 115.937 | 2451.536 | 17.819 | 9990.182 |
| $10^{-7}$ | 25 | 7.75 | 0.0026 | 12.850 | −51.461 | 102.927 | 2466.974 | 19.422 | 10371.445 |
| $10^{-8}$ | 2 | 6.25 | 0.0333 | 14.311 | −47.739 | 95.622 | 2407.372 | 20.958 | 9661.111 |
| $10^{-9}$ | <1 | 10.25 | 0.0116 | 14.753 | −45.047 | 90.102 | 2388.660 | 21.217 | 9576.258 |
| $10^{-10}$ | <1 | 5.75 | 0.0264 | 15.344 | −42.288 | 84.701 | 2272.854 | 21.828 | 9164.188 |
| $10^{-11}$ | <1 | 5.75 | 0.0475 | 16.253 | −39.750 | 79.616 | 2082.067 | 22.364 | 8430.976 |

TABLE 1D

Thermodynamic Parameters for Growth of *Bacillus subtilis* of Different Concentrations

| Dilution | cfu | $T_e$ (h) | k (min$^{-1}$) | $T_d$ (h) | $P_0$ (μW) | $P_i$ (μW) | $P_{max}$ (μW) | $T_{max}$ (h) | $H_{total}$ (μJ) |
|---|---|---|---|---|---|---|---|---|---|
| 0 | 0 | | −0.0088 | | | | 158.450 | 1.567 | 1696.003 |
| $10^{-3}$ | $10^5$ | 5.50 | 0.0127 | 8.383 | 57.614 | 230.569 | 633.049 | 11.753 | 8631.254 |
| $10^{-5}$ | 2000 | 8.25 | 0.0172 | 10.456 | 46.911 | 187.687 | 962.157 | 13.192 | 12183.089 |
| $10^{-7}$ | 20 | 10.50 | 0.1180 | 13.261 | 38.736 | 155.109 | 787.727 | 16.103 | 10216.512 |
| $10^{-8}$ | 2 | 12.00 | 0.0121 | 15.706 | 39.718 | 159.193 | 632.033 | 19.686 | 7512.225 |
| $10^{-9}$ | <1 | | −0.0057 | ND | | | 114.331 | 1.108 | 207.008 |
| $10^{-10}$ | <1 | | −0.0037 | ND | | | 64.495 | 1.672 | −174.555 |
| $10^{-11}$ | <1 | | −0.0019 | ND | | | 100.899 | 0.803 | −489.902 |

TABLE 1E

Thermodynamic Parameters for Growth of *Clostridium sporogenes* of Different Concentrations

| Dilution | cfu | $T_e$ (h) | K (min$^{-1}$) | $T_d$ (h) | $P_0$ (μW) | $P_i$ (μW) | $P_{max}$ (μW) | $T_{max}$ (h) | $H_{total}$ (μJ) |
|---|---|---|---|---|---|---|---|---|---|
| 0 | 0 | | −0.0064 | | | | 206.729 | 0.936 | 2788.582 |
| $10^{-3}$ | $10^5$ | 1.25 | 0.0563 | 5.108 | 118.721 | 475.123 | 1049.431 | 7.683 | 16584.828 |
| $10^{-5}$ | 3600 | 5.25 | 0.0117 | 9.644 | 80.822 | 323.642 | 1100.793 | 13.661 | 15832.796 |
| $10^{-7}$ | 36 | 9.00 | 0.0225 | 13.536 | 68.729 | 275.166 | 1127.010 | 17.528 | 15430.693 |
| $10^{-8}$ | 3 | 9.50 | 0.0072 | 15.242 | 63.895 | 256.033 | 1065.710 | 19.683 | 15480.996 |
| $10^{-9}$ | <1 | 12.75 | 0.0075 | 17.672 | 57.831 | 231.328 | 1078.571 | 22.269 | 15249.404 |
| $10^{-10}$ | <1 | 14.25 | 0.0088 | 18.953 | 55.945 | 223.794 | 1020.511 | 23.478 | 14994.583 |
| $10^{-11}$ | <1 | | −0.0048 | ND | | | 136.633 | 1.028 | 2111.035 |

TABLE 1F

Thermodynamic Parameters for Growth of *Dysentery bacterium* of Different Concentrations

| Dilution | cfu | $T_e$ (h) | k (min$^{-1}$) | $T_d$ (h) | $P_0$ (μW) | $P_i$ (μW) | $P_{max}$ (μW) | $T_{max}$ (h) | $H_{total}$ (μJ) |
|---|---|---|---|---|---|---|---|---|---|
| 0 | 0 | | −0.0009 | | | | 80.296 | 1.169 | 881.967 |
| $10^{-3}$ | $10^5$ | 0.75 | 2.7368 | 3.333 | 50.764 | 203.237 | 718.936 | 5.528 | 9375.730 |

TABLE 1F-continued

Thermodynamic Parameters for Growth of *Dysentery bacterium* of Different Concentrations

| Dilution | cfu | $T_e$ (h) | k (min$^{-1}$) | $T_d$ (h) | $P_0$ (μW) | $P_i$ (μW) | $P_{max}$ (μW) | $T_{max}$ (h) | $H_{total}$ (μJ) |
|---|---|---|---|---|---|---|---|---|---|
| $10^{-5}$ | 2000 | 4.25 | 0.0073 | 5.708 | 30.970 | 124.122 | 632.982 | 8.869 | 8611.000 |
| $10^{-7}$ | 26 | 7.25 | 0.0126 | 8.342 | 18.449 | 73.914 | 354.460 | 12.989 | 6975.583 |
| $10^{-8}$ | 2 | 0.75 | 2.1408 | 11.814 | 12.907 | 51.639 | 110.610 | 18.600 | 3724.997 |
| $10^{-9}$ | <1 | 12.75 | 0.0063 | 13.058 | 10.862 | 43.480 | 75.744 | 24.086 | 3135.658 |
| $10^{-10}$ | <1 | | −0.0033 | ND | | | 206.729 | 0.947 | 3220.400 |
| $10^{-11}$ | <1 | | −0.0008 | ND | | | 127.919 | 1.122 | 2380.774 |

TABLE 1G

Thermodynamic Parameters for Growth of *Aspergillus niger* of Different Concentrations

| Dilution | cfu | $T_e$ (h) | k (min$^{-1}$) | $T_d$ (h) | $P_0$ (μW) | $P_i$ (μW) | $P_{max}$ (μW) | $T_{max}$ (h) | $H_{total}$ (μJ) |
|---|---|---|---|---|---|---|---|---|---|
| 0 | 0 | | −0.0101 | | | | 161.194 | 1.003 | −108.527 |
| $10^{-3}$ | $10^4$ | 2.25 | 0.0073 | 4.750 | 26.813 | 107.258 | 180.680 | 5.733 | 2895.429 |
| $10^{-5}$ | 3000 | 4.75 | 0.0117 | 6.953 | 13.212 | 52.990 | 156.541 | 8.667 | 1898.576 |
| $10^{-7}$ | 360 | 2.75 | 0.0093 | 9.189 | 5.542 | 22.507 | 142.759 | 11.697 | 1934.208 |
| $10^{-8}$ | 3 | 3.00 | 0.0617 | 11.700 | −0.960 | 1.975 | 123.643 | 14.853 | 1173.551 |
| $10^{-9}$ | <1 | 11.50 | 0.0053 | 13.608 | −4.899 | 9.797 | 134.891 | 17.514 | 1974.932 |
| $10^{-10}$ | <1 | 14.25 | 0.0057 | 15.953 | −4.931 | 9.919 | 128.662 | 19.472 | 1976.428 |
| $10^{-11}$ | <1 | 15.50 | 0.0113 | 17.681 | −7.885 | 15.774 | 122.944 | 20.778 | 1624.164 |

TABLE 1H

Thermodynamic Parameters for Growth of *Candida albicanss* of Different Concentrations

| Dilution | cfu | $T_e$ (h) | k (min$^{-1}$) | $T_d$ (h) | $P_0$ (μW) | $P_i$ (μW) | $P_{max}$ (μW) | $T_{max}$ (h) | $H_{total}$ (μJ) |
|---|---|---|---|---|---|---|---|---|---|
| 0 | 0 | | −0.0047 | | | | 171.439 | 1.003 | 4865.695 |
| $10^{-3}$ | $10^6$ | 6.25 | 0.0056 | 36.400 | 65.756 | 263.029 | 358.032 | 52.011 | 15889.942 |
| $10^{-5}$ | $10^4$ | 6.25 | 0.0053 | 63.700 | 50.118 | 200.725 | 252.685 | 71.006 | 8759.188 |
| $10^{-7}$ | 500 | 6.25 | 0.0058 | >71.011 | 46.316 | 112.481 | 112.747 | 70.761 | 5251.484 |
| $10^{-8}$ | 48 | 6.25 | 0.0319 | >71.011 | 46.316 | 85.384 | 86.658 | 70.636 | 3965.306 |
| $10^{-9}$ | 5 | 20.00 | 0.0015 | >71.011 | 46.316 | 119.575 | 119.575 | 71.011 | 7133.872 |
| $10^{-10}$ | <1 | 20.00 | 0.0018 | >71.011 | 46.316 | 112.162 | 112.273 | 71.000 | 6628.107 |
| $10^{-11}$ | <1 | 7.25 | 0.0032 | >71.011 | 46.316 | 88.287 | 88.449 | 70.900 | 4605.575 |

The parameters of *Staphylococcus aureus* under different survival conditions are shown as follows:

TABLE 2

Thermodynamic Parameters for Growth of *Staphylococcus aureus* Under Different Conditions

| Dilution | cfu | $T_e$ (h) | k (min$^{-1}$) | $T_d$ (h) | $P_0$ (μW) | $P_i$ (μW) | $P_{max}$ (μW) | $T_{max}$ (h) | $H_{total}$ (μJ) |
|---|---|---|---|---|---|---|---|---|---|
| TM | 0 | | −0.0004 | | | | 142.725 | 1.003 | 1446.990 |
| Phys | 0 | | 0.0000 | | | | 210.286 | 1.003 | −164.582 |
| 35° C. $10^{-5}$ | $10^5$ | 10.25 | 0.0093 | 12.853 | 23.532 | 94.177 | 479.526 | 18.989 | 10094.389 |
| 35° C. $10^{-7}$ | 750 | 10.50 | 0.0074 | 15.169 | 20.825 | 83.434 | 401.608 | 23.219 | 8278.074 |
| −70° C. $10^{-5}$ | 105 | 18.00 | 0.0058 | 22.628 | 16.876 | 67.555 | 222.876 | 55.903 | 8501.300 |
| −70° C. $10^{-7}$ | 280 | 19.50 | 0.0051 | 23.694 | 17.403 | 69.617 | 169.815 | 32.350 | 8623.707 |
| 60° C. $10^{-5}$ | $10^4$ | 19.50 | 0.0004 | 37.308 | 15.657 | 62.669 | 285.059 | 52.178 | 9163.460 |
| 60° C. $10^{-7}$ | 38 | 78.50 | 0.0086 | 82.108 | 7.482 | 29.950 | 59.617 | 90.042 | 2425.452 |

According to massive data analysis and sorting up, the judgment indicators for microbial contamination under this invention is that, k≥0 is taken as the premise to detect the strains to be tested, the time duration where the difference between the detection channel Pi and the thermal power is $P_0$ greater than three times of the absolute value of $P_0$ of the blank channel at that time is taken as the time point (Time of Detection, Td) to detect the microbial contamination of the samples, which is: $T_d$=Time[$(P_i-P_0)/|P_0|\geq 3$]. Make analysis on the abovementioned experimental data based on these indices. Findings are made that:

(1) The thermograms of the growth of each strain is provided with obvious fingerprint characteristics and may be applied to the characteristic verifications for different strains; the maximum thermal power ($P_{max}$), the total thermal power ($H_{total}$) and the peak structure of the curve are stable and can most represent the difference of the characteristics of different strains.

(2) With the dilution being lowered, the peak shape of each strain thermogram is basically unchanged; and the time for the maximum thermal power ($T_{max}$) is uniformly delayed, so as the exponential growth time ($T_e$).

With the dilution of the strain being lowered, the maximum thermal powers for the *Escherichia coli* and Dysentery bacterium are lowered accordingly;

With the dilution of the strain being lowered, the detection time of each strain ($T_d$) is lowered gradually and represents a favorable linear relationship.

(3) Except that the detection time for *Candida albicans* is relatively long (greater than 36 h), other strains are basically detected within 18 h. And there're obvious linear relationships between the detection time and the concentration of the bacteria culture which shows the favorable universality and quickness of themicrocalorimetric method on detection of various microorganisms. In addition, conclusion may be drawn that the *Candida albicans* grows relatively slower; while other microorganisms growth fast under such conditions and can be quickly detected.

(4) Detection of the *Staphylococcus aureus* under different conditions: fresh culture (<18 h)<refrigerated culture (<24 h)<high temperature culture (>36 h)

(5) The result on counting of living bacteria shows that, this invention can detect various microorganisms in liquid with the concentration lower than 1 cuf. The method is provided with high sensitivity. In addition, diluted cultures for *Staphylococcus aureus, Pseudomonas aeruginosa, Aspergillus niger*, etc. with the concentration of lower than $10^{-11}$ may also be detected.

After the steps above, the fingerprint characteristic thermogram and related thermodynamic parameters for each strain are obtained and the positive judgment indices for strains are be established; such spectrums and data formulas may be used as the technical analysis data for this invention as well as standards for further tests, in other words, operations to establish standards is not necessarily to be repeated, after the standards are established, only operation procedures in Step (5) are required on samples to be tested with comparison to the standards so established.

For example, if preparation to be tested is compound herba artemisiae injection, when making the sterility test, efforts may be needed only to filter and cultivate the sample and to transcribe the thermogram of the sample in the microcalorimeter. Compared the thermogram of the sample with the positive judgment indices for strains obtained in Step (4), if there exist characteristics in accordance with the positive judgment indices for strains in the sample thermogram, it can be judged that there's microbial contamination in the sample. Then judge the type of the contaminated strains in the sample according to the strain fingerprint characteristic thermogram obtained in Step (3)

V, Inspection on the Sterility of the Preparation to be Tested

To inspect the reliability and sensitivity of the method under this invention, more than selecting the normally sterilized sample of the compound herba artemisiae injection as the sample to be tested, the following detection procedures also select the non-sterilized samples of the compound herba artemisiae injection, sub-sterilized samples, normally sterilized sample+<100 cfu *Staphylococcus aureus*, normally sterilized sample+<100 cfu *Candida albicans* as reference for the sample to be tested. Collected related data and make data analysis with the following specific operation methods:

Take the non-sterilized samples, sub-sterilized samples and normally sterilized samples of the compound herba artemisiae injection, 200 mL respectively; rinse with water solution of 0.1% for three times, 100 mL each time respectively; empty the cleaning liquid; inject 10 mL fluid thioglycollate culture medium into the ampoule; take additional samples as mentioned above and process according to the steps above, introduce 10 mL Modified martin medium after the cleaning liquid is emptied.

Take additional two normally sterilized sample (200 mL each) and process according to the steps above, introduce 10 mL fluid thioglycollate culture medium and 10 mL Modified martin medium respectively after the cleaning liquid is emptied; add the *Staphylococcus aureus* smaller than 100 cfu into the fluid thioglycollate culture medium, and add diluted *Candida albicans* culture of smaller than 100 cuf into the Modified martin medium as positive reference.

Place each ampoule in the corresponding microcalorimeter; record the thermograms. The transcribed thermograms are shown in FIG. 10. Data drawn from each curve is listed in the following table, where, k: the offsetting of thermogram for each 15 min; $T_e$: occurrence time of k≥0; Td: detection time of microorganism; $P_{max}$: maximum thermal power; $T_{max}$: time of maximum thermal power; $H_{total}$: total thermal power.

TABLE 3

Parameter Drawing and Result Judgment of the Sterility Test for Compound *Herba Artemisiae* Injection by Method Under This Invention

| Sample | $T_e$/h | k/min$^{-1}$ | $T_d$/h | $P_{max}$/µW | $T_{max}$/h | $H_{total}$/µJ |
|---|---|---|---|---|---|---|
| normally sterilized sample + TM | | −0.0036 | | | | |
| *Staphylococcus aureus* + TM | 2 | 597.813 | 4 | 1449.653 | 5.017 | 12426.624 |
| non-sterilized samples + TM | 5 | 1050.195 | 9 | 2149.121 | 9.708 | 16361.561 |
| sub-sterilized samples + TM | 5.5 | 1101.199 | 10 | 1274.160 | 10.392 | 8741.553 |
| normally sterilized sample + Martin | | −0.0041 | | | | |
| *Candida albicans* + Martin | 4.5 | 670.254 | 15.5 | 767.432 | 17.308 | 10052.645 |

TABLE 3-continued

Parameter Drawing and Result Judgment of the Sterility Test for Compound
Herba Artemisiae Injection by Method Under This Invention

| Sample | $T_e$/h | k/min$^{-1}$ | $T_d$/h | $P_{max}$/μW | $T_{max}$/h | $H_{total}$/μJ |
|---|---|---|---|---|---|---|
| non-sterilized samples + Martin | 6 | 297.024 | 10 | 1705.366 | 10.614 | 12971.938 |
| sub-sterilized samples + Martin | 6.5 | 219.156 | 10.5 | 616.537 | 13.208 | 5863.318 |

Data Analysis (1) According to the thermogram, the normal sample channel (normal sample+fluid thioglycollate culture medium, normal sample+Modified martin medium) represents a trend of gentle lowering. According to the thermodynamic parameters, the k value of the normal sample is continuously minus, representing that there're no microbial contamination and the culture medium sterility is favorable.

(2) According to the thermogram, the growth of the microorganism in the positive reference channel (*Staphylococcus aureus*+fluid thioglycollate culture medium, *Candida albicans*+Modified martin medium) is favorable, representing that such condition is suitable for the sterility test of the compound herba artemisiae injection and is provided with relatively favorable sensitivity.

(3) The microbial contaminations in the non-sterilized samples and sub-sterilized samples are all detected within 10.5 h. According to the thermodynamic parameters, the $P_{max}$ values in the non-sterilized samples are higher than those in the sub-sterilized samples, which indicates that the level of contamination is relatively higher as well as the sensitivity of such sterility test method on the difference in the contamination degrees of the samples.

The above are the steps for sterility detection with the method under this invention as well as the experimental data obtained accordingly. To make comparison with the current technologies, the sterility test data with bacteria collection observation method under the same experimental conditions provided above. And comparison is made with the experimental data under this invention.

1, Comparison of the time required to detect the microorganism with the two methods for different strains under different concentrations:

TABLE 4A

Summary Table for Types and Cultivation Conditions of Various Microorganisms

| Strain | Representative microorganism type | Cultivation temperature | Applicable culture medium |
|---|---|---|---|
| Staphylococcus aureus | Aerobic Gram positive bacteria | 35° C. | TM |
| Pseudomonas aeruginosa | aerobic Gram-negative bacteria | 35° C. | TM |
| Escheichia coli | Gram negative facultative anaerobe | 35° C. | TM |
| Shigella dysenteriae | Gram negative facultative anaerobe | 35° C. | TM |
| Bacillus subtilis | aerobic bacillus | 35° C. | TM |
| Clostridium sporogenes | anaerobe | 35° C. | TM |
| Candida albicans | Microzyme | 28° C. | Martin |
| Aspergillus niger | Fungus | 28° C. | Martin |
| 35° C. Staphylococcus aureus | Fresh culture | 35° C. | TM |
| −70° C. Staphylococcus aureus | Low temperature culture | 35° C. | TM |
| 50° C. Staphylococcus aureus | High temperature culture | 35° C. | TM |

TABLE 4B

Table for Detection Time of Various Bacterium with Method Under This Invention

| Strain | dilution | | | | | | |
|---|---|---|---|---|---|---|---|
| | $10^{-3}$ | $10^{-5}$ | $10^{-7}$ | $10^{-8}$ | $10^{-9}$ | $10^{-10}$ | $10^{-11}$ |
| Staphylococcus aureus | 10.300 | 10.539 | 10.864 | 10.994 | 11.206 | 11.594 | 11.772 |
| Pseudomonas aeruginosa | 0.817 | 3.697 | 5.469 | 13.508 | 23.372 | ND | ND |
| Escheichia coli | 9.833 | 11.614 | 12.850 | 14.311 | 14.753 | 15.344 | 16.253 |
| Shigella dysenteriae | 5.108 | 9.644 | 13.536 | 15.242 | 17.672 | 18.953 | ND |
| Bacillus subtilis | 3.333 | 5.708 | 8.342 | 11.814 | 13.058 | ND | ND |
| Clostridium sporogenes | 8.383 | 10.456 | 13.261 | 15.706 | ND | ND | ND |
| Candida albicans | 36.400 | 63.700 | >71.011 | >71.011 | >71.011 | >71.011 | >71.011 |
| Aspergillus niger | 4.750 | 6.953 | 9.189 | 11.700 | 13.608 | 15.953 | 17.681 |
| 35 Staphylococcus aureus | | 12.853 | 15.169 | | | | |
| −70 Staphylococcus aureus | | 22.628 | 23.694 | | | | |
| 60 Staphylococcus aureus | | 37.308 | 82.108 | | | | |

TABLE 4C

Table for Detection Time of Various Bacterium
with Bacteria Collection Observation Method

| strain | dilution | | | | | | |
|---|---|---|---|---|---|---|---|
| | $10^{-3}$ | $10^{-5}$ | $10^{-7}$ | $10^{-8}$ | $10^{-9}$ | $10^{-10}$ | $10^{-11}$ |
| Staphylococcus aureus | 15 | 16 | 17.5 | 18 | 18.5 | 19.5 | ND |
| Pseudomonas aeruginosa | 10.5 | 12 | 14 | 16 | 23 | ND | ND |
| Escheichia coli | 15 | 17 | 18.5 | 24 | 28 | 32 | ND |
| Shigella dysenteriae | 13 | 15 | 17 | 19.5 | 21.5 | ND | ND |
| Bacillus subtilis | 11.5 | 12.5 | 13.5 | 17.5 | 23.5 | ND | ND |
| Clostridium sporogenes | 14.5 | 16 | 18.5 | 22.5 | ND | ND | ND |
| Candida albicans | 68.5 | ND | ND | ND | ND | ND | ND |
| Aspergillus niger | 14 | 16.5 | 18.5 | 21 | 23.5 | 28 | ND |
| 35° C. Staphylococcus aureus | | 18 | 25 | | | | |
| −70° C. Staphylococcus aureus | | 36 | 43 | | | | |
| 60° C. Staphylococcus aureus | | 82 | ND | | | | |

According to the results: (1) Other than *Candida albicans*, though the detection time of other microorganisms under bacteria collection observation method is smaller than 36 h, the average detection time is longer than that of the microcalorimetric method (concentrated in 0-18 h under microcalorimetric method and 10-36 hours under the bacteria collection observation method); (2) The minimum dilution detected under bacteria collection observation method is $10^{-10}$ and the microorganism dilution of $10^{-11}$ dilution is not available; meanwhile, the minimum concentration detected is higher compared with that of the microcalorimetric method, the sensitivity is lower than that of the microcalorimetric method; (3) No obvious turbidity may occur during the detection of the *Candida albicans*; and it is hard to judge whether there's microorganism growing accurately by bacteria collection observation method (4) The detection time of the diluted cultures of *Staphylococcus aureus* stored under low temperature (−70° C.) and high temperature (60° C.) under the bacteria collection observation method is longer than that of the microcalorimetric method, and the diluted culture of $10^{-8}$ under 60° C. is not detected; (5) The microorganism strain selected involves common microorganism types in nature such as aerobe/anaerobe/facultative bacteria, Gram positive bacteria/Gram-negative bacteria, *bacillus*/microzyme/fungus, etc. (also common microbial contamination sources); while the above-mentioned microorganisms can be detected by the microcalorimetric method, which shows that such method is provided with favorable universality and can meet the requirements of the sterility test.

2, Make sterility test with compound herba artemisiae injection as the sample, with comparison of the results by the two detection methods as follows:

The judgment results with the method under this invention are shown in Table 3.

The judgment results with the bacteria collection observation method are shown in the following table.

TABLE 5

Judgment Results of the Sterility Test for Compound *Herba Artemisiae* Injection by Bacteria Collection Observation Method

| Sample | Observation time (h) | | | | | | | | | | | |
|---|---|---|---|---|---|---|---|---|---|---|---|---|
| | 0 | 3 | 6 | 9 | 12 | 15 | 18 | 24 | 48 | 72 | 96 | 120 |
| Normally sterilized sample + TM | − | − | − | − | − | − | − | − | − | − | − | −a |
| Staphylococcus aureus + TM | − | − | − | ± | + | + | + | + | + | + | + | + |
| Non-sterilized samples + TM | − | − | − | − | ± | + | + | + | + | + | + | + |
| Sub-sterilized samples + TM | − | − | − | − | − | − | ± | + | + | + | + | + |
| Normally sterilized sample + Martin | − | − | − | − | − | − | − | − | − | − | − | − |
| Candida albicans + Martin | − | − | − | − | − | − | − | − | − | ± | ± | ± |
| Non-sterilized samples + Martin | − | − | − | − | ± | ± | + | + | + | + | + | + |
| Sub-sterilized samples + Martin | − | − | − | − | − | − | − | ± | + | + | + | + |

Where, "−": not detected microbial contamination; "±": accurate judgment not available; "+": microbial contamination detected.

The summary and comparison of the time required to accurately detect the microbial contamination by the two methods are shown as follows:

TABLE 6

Comparison Table of Time Required to Detect Microbial Contamination in Compound Herba Artemisiae Injection by Method Under This Invention and Bacteria Collection Observation Method

| sample | Detection time (h) | |
|---|---|---|
| | microcalorimetric method | bacteria collection observation method |
| normally sterilized sample + TM | | |
| *Staphylococcus aureus* + TM | 4 | 12 |
| non-sterilized samples + TM | 9 | 15 |
| sub-sterilized samples + TM | 10 | 24 |
| normally sterilized sample + Martin | | |
| *Candida albicans* + Martin | 15.5 | Unavailable for accurate determination |
| non-sterilized samples + Martin | 10 | 18 |
| sub-sterilized samples + Martin | 10.5 | 48 |

According to the results, compared with the bacteria collection observation method, the method under this invention is more quick and sensitive. And the sensitivity to detect the microbial contamination of turbidity of the culture medium caused by not obvious growth (for example, *Candida albicans* and *Bacillus subtillis*) is relatively higher.

Overall comparison and summary between the method under this invention and bacteria collection observation method are detailed in the following table:

TABLE 7

Comparison on Data Detected By Microcalorimetric Method and Bacteria Collection Observation Method

| Item | Microcalorimetric Method | Bacteria Collection Observation Method |
|---|---|---|
| Timeliness | Concentrated from 0 to 18 h and within 72 h for bacteria growing slowly (*Candida albicans*) | Distributed from 10 to 36 h, relatively hard to detect bacteria growing slowly (the culture medium of *Candida albicans* is not turbid) |
| Sensitivity | Capable to detect the growth of microorganism with the dilution of lower than $10^{-11}$ (1 cfu) dilution | Relatively low (generally not available to detect $10^{-10}$, $10^{-11}$ dilution) |
| Quantifiability | Growth thermograms, quantitive thermodynamic parameters and standard formulas for the detection | Subjective judgment by visual observation |
| Accuracy | Accurate result judgment and can effectively avoid false negative/positive | Relatively hard to judge the false positive results caused by turbidity of culture medium caused not by the growth of microorganism and false negative caused by the failure of turbidity caused by the growth of microorganism. |
| Fingerprint Characteristic | Provide overall process microorganism growth state curve for the detection, provided with relatively favorable fingerprint characteristics, applicable for preliminary judgment for the types of the contaminant | Discontinued observation at fixed time, relatively hard to provide fingerprint information for related characteristics |
| Automation | Detect the thermogram of the sample automatically, automatically judge the sterility conditions of the sample, provide the pre-warning information with high level of automation | Requiring repeated observations, high workload, easy for misjudgment and secondary contamination, poor level of automation |

According to the comparison above, compared with traditional bacteria collection observation method, the microcalorimetric method under this invention for sterility test is quicker and more sensitive. It is provided with relatively high automation level and objectiveness and may be used as a new approach for sterility test.

Specific Implementation Method 2: Same as Step (1) to Step (4) in the Specific Implementation Method 1.

During the operations of sample filtration and culture medium injection in Step (5), to isolate the external environment (to avoid false positive judgment by secondary contamination) and meet the requirements of enrichments of the microorganism and meanwhile eliminating the bacteriostatic performance of the products, a fully-enclosed bacteria collecting ampoule incubator is used for this implementation method, with structures and instructions as follows:

As shown in FIG. 12, a fully-enclosed bacteria collecting ampoule incubator includes the bacteria collecting ampoule system, the sample and liquid feeding system and the peristalsis liquid discharge system. The sample and liquid feeding system is connected with the bacteria collecting ampoule system by liquid intake tube 4; and the bacteria collecting ampoule system is connected with the peristalsis liquid discharge system by liquid drainage tube 5.

Optimized structure: the bacteria collecting ampoule system includes an ampoule bottle body 1, seal and fix the rubber sealing plug 3 on the mouth of the ampoule bottle body; the liquid intake tube; the liquid intake tube 4, liquid drainage tube 5 and gas discharge tube 6 are extended into the ampoule bottle body after penetrating the rubber sealing plug; provide a built-in filter 2 in the ampoule bottle body; lay the filter membrane 15 at the bottom of the filter; connect the top of the filter with the liquid intake tube mouth in the ampoule bottle; the liquid drainage tube mouth was extended to the bottom of the ampoule bottle across the filter; the filter membrane may be set to different materials according to different objects to be filtered. Respectively install the liquid intake control 7, liquid discharge control valve 8 and gas discharge control valve 17 on the liquid intake tube, liquid drainage tube and gas discharge tube out of the ampoule bottle body; connect the air filter 16 on top of the gas discharge tube.

Optimized structure: sample and liquid feeding system includes the sample/culture medium container 12 and liquid intake device with air filter 10.

Optimized structure: peristalsis liquid discharge system includes a peristaltic pump 13; connect the outlet of the peristaltic pump to the liquid discharge collector 14.

Optimized structure: Install a liquid intake tube connector 11 on the liquid intake tube between the liquid intake control and the sample and liquid feeding system; by disconnecting the tube connector, the sample and liquid feeding system may be separated from the bacteria collecting ampoule system; install the liquid drainage tube connector 18 on the liquid drainage tube between the liquid discharge control valve and peristalsis liquid discharge system; by disconnecting the tube connector, the peristalsis liquid discharge system may be separated from the bacteria collecting ampoule system.

The liquid intake tube connector and liquid drainage tube connector are plug type; the plugs of the liquid intake tube connector and the liquid drainage tube connector may be made butt joint to form the enclosed tube connector 19.

After the procedures of filtration in the bacteria collecting ampoule incubator and the injection of the culture medium, separate the sample and liquid feeding system with the bacteria collecting ampoule system from the plug of the liquid drainage tube connector 18; the make butt joint of the plugs of the liquid intake tube connector and the liquid drainage tube connector to form the enclosed tube connector 19; keep the bacteria collection in a sealed condition, as shown in FIG. 13.

Optimized structure: Graduation line 9 is marked on the ampoule bottle body. The precisions may be determined according to actual requirements, for example, graduation lines such as 5 mL, 10 mL, and 15 mL.

Optimized structure: ampoule bottle body is glass structure or hard plastic structure. Transparent materials may guarantee the accuracy of external observation.

Optimized structure: The liquid intake control, liquid discharge control valve and gas discharge control valve are Bayonet valves.

Optimized structure: The liquid intake tube, liquid drainage tube and gas discharge tube are silica gel tubes.

Optimized structure: gas discharge tube is a stainless pinhead with air filtration device on the top, hallow at the end and with openings on the side wall.

In addition, this invention also provides a deformed structure from the liquid intake tube.

As shown in FIG. 14 and FIG. 15, the extended part of the liquid intake tube into the ampoule bottle body is a diverging pipe 20 which is thin on top and thick at bottom; the filter is fixed at the lower end of the diverging pipe. The external surface of the upper end of the diverging pipe is screw structure 21; an internal thread joint 22 is fastened on the mouth of the liquid intake tube on the lower surface of the rubber sealing plug; the diverging pipe may be connected with such internal thread joint by the screw structure.

Instructions for the abovementioned fully-enclosed bacteria collecting ampoule incubator:

(1), Connect the sample and liquid feeding system, the bacteria collecting ampoule system, the peristalsis liquid discharge system in order, in other words, connect the liquid intake device 10 with the sample/culture medium container 12; make joint-butt of the plug of the liquid intake tube connector 11. The sample to be tested is in the sample/culture medium container 12; then connect the plug of the liquid drainage tube connector 18;

(2), Close gas discharge control valve 17; open liquid intake control 7, liquid discharge control valve 8, peristaltic pump 13, adjust the flow rate, slowly filter the sample and discharge the liquid; After the abovementioned steps are finished, open gas discharge channel control valve 17, close peristaltic pump 13, liquid intake control 7, liquid discharge control valve 8;

(3), Replace sample/culture medium container to the sterile cleaning liquid container, close gas discharge channel control valve 17, open liquid intake control 7, liquid discharge control valve 8, peristaltic pump 13, adjust the flow rate, clean the filter membrane and discharge the waste liquid;

(4), Close peristaltic pump 13, liquid discharge control valve 8, liquid intake control 7, open gas discharge control valve 17, replace the sample in the sample/culture medium container 12 to corresponding culture medium;

(5), Close gas discharge control valve 17, open liquid discharge control valve 8, peristaltic pump 13, make the bottle in a negative pressure state; vacuum the filter membrane 15 till it's broken, connect filter 2 into the bottle body;

(6), Close liquid discharge control valve 8, peristaltic pump 13, open liquid intake control 7, add culture medium to corresponding graduation, close liquid intake control 7;

(7), If a certain proportion of air is required to boost fast growth of the microorganism during the process of cultivation, open gas discharge control valve 17 and inject air into the bacteria collecting ampoule incubator according to specific proportion; then plug out the gas discharge channel 6; if no air is required for cultivation, directly pull out the gas discharge channel 6 after Step ⑥;

(8), Open the plugs of the liquid intake tube connector 11 and liquid drainage tube connector 18; connect the plugs of the two tube connector to form the enclosed tube connector 19; keep the bacteria collecting ampoule incubator in a sealed state;

(9), Place the sealed bacteria collecting ampoule incubator into corresponding detection apparatus/environment; obtain the detection results for the sample.

Specific instructions for sterility test with fully-enclosed bacteria collection ampoule on the compound herba artemisiae injection preparation to be tested:

(1), Connect liquid intake device 10 onto sample/culture medium container 12; make butt-joint with the plug of the liquid intake tube connector 11; the sample of compound herba artemisiae injection is in the sample/culture medium container 12; then make butt-joint of the plug of liquid drainage tube connector 18;

(2), Close gas discharge control valve 17, open liquid intake control 7, liquid discharge control valve 8, peristaltic pump 13, adjust the flow rate, slowly filter the compound herba artemisiae injection sample and discharge the liquid; after the steps mentioned above; open gas discharge channel control valve 17, close peristaltic pump 13, liquid intake control 7, liquid discharge control valve 8;

(3), Replace compound herba artemisiae injection container with sterile cleaning liquid container, close gas discharge channel control valve 17, open liquid intake control 7, liquid discharge control valve 8 and peristaltic pump 13, adjust the flow rate, rinse the filter membrane and discharge the waste liquid;

(4), Close peristaltic pump 13, liquid discharge control valve 8, liquid intake control 7, open gas discharge control valve 17, replace the injection sample in the sample/culture medium container 12 with fluid thioglycollate culture medium or modified martin medium;

(5), Close gas discharge control valve 17, open liquid discharge control valve 8, peristaltic pump 13, make the bottle in a negative pressure state; vacuum the filter membrane 15 till it's broken, connect filter 2 into the bottle body;

(6), Close liquid discharge control valve 8, peristaltic pump 13, open liquid intake control 7, add culture medium to corresponding graduation, close liquid intake control 7;

(7), Open gas discharge control valve 17, inject air to the bacteria collecting ampoule incubator, then plug out the gas discharge channel 6;

(8), Open the plugs of the liquid intake tube connector 11 and liquid drainage tube connector 18; connect the plugs of the two tube connector to form the enclosed tube connector 19; keep the bacteria collecting ampoule incubator in a sealed state;

(9) Place the sealed bacteria collecting ampoule incubator into the microcalorimeter; obtain the thermogram of the compound herba artemisiae injection sample The technological solutions mentioned above are just optimized ones. Any possible variances on part(s) thereof by technicians within this technical field following the principles of this invention shall be included into the scope of protection of this invention.

The invention claimed is:

1. A method for testing sterility of a sample comprising the steps of:
   (1) preparing bacterial cultures comprising the steps of: cultivating different bacterial strains in a sterile culture medium to obtain bacterial cultures with different concentrations and different survival conditions as positive controls for recording fingerprint characteristic thermograms of the different bacterial strains; wherein the method for obtaining the bacterial cultures of different concentrations comprises: washing fresh bacteria cultures to obtain eluents, diluting the eluents with 0.9% sterile sodium chloride solution to produce a series of 10-fold dilutions; wherein the method for obtaining the bacterial cultures of different survival conditions comprises: filtering and eluting the bacterial cultures to obtain eluents, placing the eluents in a freezer at $-70°$ C. and in a water bath at $60°$ C., respectively, for 2 h, and diluting the eluents with 0.9% sterile sodium chloride solution to produce a series of 10-fold dilutions;
   (2) recording the fingerprint characteristic thermograms of the different bacterial strains as diagnostic characteristics, wherein the recording comprises: placing the bacterial cultures obtained in Step (1) in a microcalorimeter under conditions suitable for growth of said bacterial cultures, recording the thermograms at different concentrations and under different survival conditions of the different bacterial strains to obtain the fingerprint characteristic thermograms of the different bacterial strains;
   (3) obtaining the thermodynamic parameters from the thermograms obtained in Step (2), and determining positive identification time indices for the bacterial strains; wherein the thermodynamic parameters comprise a time-dependent positive detection channel thermal power $P_i$ and a corresponding blank control channel thermal power $P_0$, the maximum thermal power $P_{max}$, time required to reach the maximum thermal power $T_{max}$, total heat production $H_{total}$, and a slope k obtained from a 15-min segment on each exponential growth curve; and a positive identification time index for a strain obtained by recording the occurrence time for k≥0, which is an essential condition for determining microbial contamination of a sample, and establishing a positive identification time index for the growth of the microorganism; and
   (4) assessing sterility of the sample to be tested comprising the steps of: filtering the sample to be tested, rinsing products collected on the filter with a sterile solution; mixing the filtrate of the sample with the culture medium, putting the mixture into the detection channel of the microcalorimeter, recording a thermogram; comparing with the fingerprint characteristic thermograms for the different bacterial strains from Step (2) and the positive identification time indices for the different bacterial strains from Step (3), and determining the microbial contamination of the tested sample using the positive identification time indices for the growth of the microorganism in Step (3) as follows:

$$T_d = \text{Time}[(P_i - P_0)/|P_0| \geq 3]$$

wherein the time duration where the difference between the thermal power of the detection channel $P_i$ and the thermal power $P_0$ is greater than three times of the absolute value of $P_0$ of the blank channel, taken as the detection time point ($T_d$), indicates microbial contamination of the sample.

2. The method of claim 1 wherein the step of placing the bacterial culture into the microcalorimeter in Step (2) comprises:
   obtaining serially diluted cultures of $10^{-3}$, $10^{-5}$, $10^{-7}$, $10^{-8}$, $10^{-9}$, $10^{-10}$, $10^{-11}$ fold dilutions, respectively, for each strain using the sterile culture medium according to the method stated in Step (1);

adding an equal volume of the diluted cultures of different concentration for each strain into the positive detection channel of the microcalorimeter; and adding another aliquot of the sterile culture medium in the blank control channel of the microcalorimeter.

\* \* \* \* \*